United States Patent
DelloStritto et al.

(10) Patent No.: US 9,872,087 B2
(45) Date of Patent: Jan. 16, 2018

(54) PLATFORM FOR PATIENT MONITORING

(71) Applicant: Welch Allyn, Inc., Skaneateles Falls, NY (US)

(72) Inventors: James J. DelloStritto, Jordan, NY (US); Atanu Roy Chowdhury, Syracuse, NY (US); Harrish Mugundhan, Syracuse, NY (US); Adam P. Vallee, Cato, NY (US); Laleh Rabieirad, Ithaca, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 133 days.

(21) Appl. No.: 14/488,917

(22) Filed: Sep. 17, 2014

(65) Prior Publication Data

US 2015/0334474 A1    Nov. 19, 2015

Related U.S. Application Data

(62) Division of application No. 12/907,873, filed on Oct. 19, 2010, now abandoned.

(51) Int. Cl.
*H04Q 9/00* (2006.01)
*A61B 5/00* (2006.01)
(Continued)

(52) U.S. Cl.
CPC ............ *H04Q 9/00* (2013.01); *A61B 5/0015* (2013.01); *G06F 17/30312* (2013.01);
(Continued)

(58) Field of Classification Search
CPC .. G06F 19/34; G06F 19/3406; G06F 19/3418; G06F 17/30312; G06F 17/30864;
(Continued)

(56) References Cited

U.S. PATENT DOCUMENTS 5,188,969 A    2/1993  Arai
5,231,990 A    8/1993  Gauglitz
(Continued)

FOREIGN PATENT DOCUMENTS

DE    4408300 A1    9/1994
DE    69228423 T2    9/1999
(Continued)

OTHER PUBLICATIONS

4000 Avant; Wearable Digital Pulse Oximetry with Bluetooth® Wireless Technology; © 2005 Nonin Medical, Inc.; 2 pages.
(Continued)

*Primary Examiner* — Hai Phan
*Assistant Examiner* — Franklin Balseca
(74) *Attorney, Agent, or Firm* — Merchant & Gould, P.C.

(57) ABSTRACT

A system for storing data collected by a body-worn sensor includes a central processing unit (CPU) that is configured to control operation of a gateway device; and one or more computer readable data storage media storing software instructions that, when executed by the CPU, cause the gateway device to: receive a MAC address of a new sensor and a protocol version associated with the new sensor from a server; attempt to contact the new sensor using the protocol version and the MAC address; when a response is received, send the response to the server for validation; when the response is validated by the server, establish communications with the new sensor; and forward data from the new sensor to a second server.

5 Claims, 17 Drawing Sheets

(51) Int. Cl.
  *G06F 17/30* (2006.01)
  *G06F 19/00* (2011.01)
  *H04L 29/08* (2006.01)

(52) U.S. Cl.
  CPC .. *G06F 17/30864* (2013.01); *G06F 17/30876* (2013.01); *G06F 19/322* (2013.01); *G06F 19/3406* (2013.01); *G06F 19/3418* (2013.01); *G06F 19/3487* (2013.01); *H04L 67/12* (2013.01); *A61B 5/0002* (2013.01); *A61B 5/0022* (2013.01); *A61B 5/0026* (2013.01)

(58) Field of Classification Search
  CPC ............. G06F 17/30876; G06F 19/322; G06F 19/3487; A61B 5/00; A61B 5/0002; A61B 5/0004; A61B 5/0022; A61B 5/0024; A61B 5/0026; A61B 5/0015; H04Q 2209/00; H04Q 2209/10; H04Q 2209/20; H04Q 2209/40; H04Q 2209/43; H04Q 2209/70; H04Q 9/00; H04L 67/12
  USPC .................... 340/870.01, 870.02, 870.07
  See application file for complete search history.

(56) References Cited

U.S. PATENT DOCUMENTS

| | | | |
|---|---|---|---|
| 5,301,270 A | 4/1994 | Steinberg | |
| 5,392,390 A | 2/1995 | Crozier | |
| 5,410,695 A | 4/1995 | Frey | |
| 5,579,775 A | 12/1996 | Dempsey | |
| 5,666,553 A | 9/1997 | Crozier | |
| 5,687,734 A | 11/1997 | Dempsey | |
| 5,701,423 A | 12/1997 | Crozier | |
| 5,715,314 A | 2/1998 | Payne | |
| 5,860,917 A | 1/1999 | Comanor | |
| 5,862,377 A | 1/1999 | Lee | |
| 5,882,300 A | 3/1999 | Malinouskas | |
| 5,906,004 A | 5/1999 | Lebby | |
| 5,909,492 A | 6/1999 | Payne | |
| 5,924,074 A | 7/1999 | Evans | |
| 5,960,411 A | 9/1999 | Hartman | |
| 6,014,651 A | 1/2000 | Crawford | |
| 6,025,841 A | 2/2000 | Finkelstein | |
| 6,057,758 A | 5/2000 | Dempsey | |
| 6,080,690 A | 6/2000 | Lebby | |
| 6,208,345 B1 | 3/2001 | Sheard | |
| D439,981 S | 4/2001 | Kasabach | |
| 6,220,510 B1 | 4/2001 | Everett | |
| 6,243,765 B1 | 6/2001 | Raab | |
| 6,266,340 B1 | 7/2001 | Pickett | |
| 6,266,645 B1 | 7/2001 | Simpson | |
| 6,289,238 B1 | 9/2001 | Besson | |
| 6,308,113 B1 | 10/2001 | Nowlin | |
| D451,604 S | 12/2001 | Kasabach | |
| 6,366,578 B1 | 4/2002 | Johnson | |
| 6,400,711 B1 | 6/2002 | Pounds | |
| 6,414,698 B1 | 7/2002 | Lovell | |
| 6,446,253 B1 | 9/2002 | Mellmer | |
| 6,452,597 B1 | 9/2002 | Goldberg | |
| 6,453,356 B1 | 9/2002 | Sheard | |
| 6,456,305 B1 | 9/2002 | Qureshi | |
| 6,469,714 B2 | 10/2002 | Buxton | |
| 6,496,705 B1 | 12/2002 | Ng | |
| 6,527,711 B1 | 3/2003 | Stivoric | |
| 6,544,173 B2 | 4/2003 | West | |
| 6,560,222 B1 | 5/2003 | Pounds | |
| 6,577,893 B1 | 6/2003 | Besson | |
| 6,605,038 B1 * | 8/2003 | Teller | A61B 5/411 128/904 |
| 6,616,606 B1 | 9/2003 | Petersen | |
| 6,633,848 B1 | 10/2003 | Johnson | |
| 6,643,541 B2 | 11/2003 | Mok | |
| 6,647,432 B1 | 11/2003 | Ahmed | |
| 6,678,413 B1 | 1/2004 | Liang et al. | |
| 6,704,804 B1 | 3/2004 | Wilson | |
| 6,714,946 B1 | 3/2004 | Kanai | |
| 6,723,046 B2 | 4/2004 | Lichtenstein | |
| 6,757,682 B1 | 6/2004 | Naimark | |
| 6,785,691 B1 | 8/2004 | Hewett | |
| 6,785,891 B1 | 8/2004 | Allen | |
| 6,799,165 B1 | 9/2004 | Boesjes | |
| 6,840,904 B2 | 1/2005 | Goldberg | |
| 6,857,123 B1 | 2/2005 | Nuxoll | |
| 6,915,957 B2 | 7/2005 | Kisliakov | |
| 6,920,633 B1 | 7/2005 | Venkatraman | |
| 6,934,740 B1 | 8/2005 | Lawande | |
| 6,940,403 B2 | 9/2005 | Kail | |
| 6,988,989 B2 | 1/2006 | Weiner | |
| 7,004,907 B2 | 2/2006 | Banet | |
| 7,006,614 B2 | 2/2006 | Feinberg | |
| 7,020,508 B2 | 3/2006 | Stivoric | |
| 7,092,958 B2 | 8/2006 | Hempstead | |
| 7,129,836 B2 | 10/2006 | Lawson | |
| 7,137,099 B2 | 11/2006 | Knight | |
| 7,153,262 B2 | 12/2006 | Stivoric | |
| 7,154,398 B2 | 12/2006 | Chen | |
| 7,171,425 B2 | 1/2007 | Cazemier | |
| 7,177,859 B2 | 2/2007 | Pather | |
| 7,179,228 B2 | 2/2007 | Banet | |
| 7,188,158 B1 | 3/2007 | Stanton | |
| 7,200,779 B1 | 4/2007 | Coss | |
| 7,206,630 B1 | 4/2007 | Tarler | |
| 7,238,159 B2 | 7/2007 | Banet | |
| 7,249,159 B1 | 7/2007 | Horvitz | |
| 7,261,690 B2 | 8/2007 | Teller | |
| 7,285,090 B2 | 10/2007 | Stivoric | |
| 7,294,105 B1 | 11/2007 | Islam | |
| 7,299,159 B2 | 11/2007 | Nanikashvili | |
| 7,299,240 B1 | 11/2007 | Crozier | |
| 7,310,673 B2 | 12/2007 | Zhu | |
| 7,318,009 B2 | 1/2008 | Beam | |
| 7,375,647 B2 | 5/2008 | Evans | |
| 7,386,672 B2 | 6/2008 | Casazza | |
| 7,390,299 B2 | 6/2008 | Weiner | |
| 7,396,330 B2 | 7/2008 | Banet | |
| 7,407,484 B2 | 8/2008 | Korman | |
| 7,409,403 B1 | 8/2008 | Faraldo | |
| 7,433,888 B2 | 10/2008 | Hunter | |
| 7,439,856 B2 | 10/2008 | Weiner | |
| 7,448,996 B2 | 11/2008 | Khanuja | |
| 7,469,250 B2 | 12/2008 | Bazot | |
| 7,481,772 B2 | 1/2009 | Banet | |
| 7,487,512 B2 | 2/2009 | Brunswig | |
| 7,493,140 B2 | 2/2009 | Michmerhuizen | |
| 7,502,643 B2 | 3/2009 | Farringdon | |
| 7,509,672 B1 | 3/2009 | Horwitz | |
| 7,515,043 B2 | 4/2009 | Welch | |
| 7,515,044 B2 | 4/2009 | Welch | |
| 7,526,437 B1 | 4/2009 | Cue | |
| 7,526,484 B2 | 4/2009 | El-Shimi | |
| 7,542,878 B2 | 6/2009 | Nanikashvili | |
| 7,542,980 B2 | 6/2009 | Tsyganskiy | |
| 7,546,335 B2 | 6/2009 | Moeller | |
| 7,559,902 B2 | 7/2009 | Ting et al. | |
| 7,586,908 B2 | 9/2009 | Nelson | |
| 7,603,427 B1 | 10/2009 | Horvitz | |
| 7,610,404 B2 | 10/2009 | Scott | |
| 7,613,702 B2 | 11/2009 | Horvitz | |
| 7,613,721 B2 | 11/2009 | Horvitz | |
| 7,613,722 B2 | 11/2009 | Horvitz | |
| 7,616,110 B2 | 11/2009 | Crump | |
| 7,647,298 B2 | 1/2010 | Adya | |
| 7,657,596 B2 | 2/2010 | Veselov | |
| 7,658,716 B2 | 2/2010 | Banet | |
| 7,680,767 B2 | 3/2010 | Adya | |
| 7,698,276 B2 | 4/2010 | Seshadri | |
| 7,702,638 B2 | 4/2010 | Tsyganskiy | |
| 7,720,879 B2 | 5/2010 | Tsyganskiy | |
| 7,725,476 B2 | 5/2010 | Waggoner | |
| 7,743,391 B2 | 6/2010 | Balaji | |
| 7,752,603 B2 | 7/2010 | Harutunian | |
| 7,788,250 B2 | 8/2010 | Salman | |
| 9,619,621 B2 * | 4/2017 | Dicks | G06F 19/3418 |

(56) References Cited

U.S. PATENT DOCUMENTS

| | | |
|---|---|---|
| 2001/0000811 A1 | 5/2001 | May |
| 2002/0038368 A1 | 3/2002 | Kojima |
| 2002/0046301 A1 | 4/2002 | Shannon |
| 2002/0065919 A1 | 5/2002 | Taylor |
| 2002/0073241 A1 | 6/2002 | Gilbert |
| 2002/0082893 A1 | 6/2002 | Barts |
| 2002/0089526 A1 | 7/2002 | Buxton |
| 2002/0188629 A1 | 12/2002 | Burfoot |
| 2003/0023506 A1 | 1/2003 | Skibinski |
| 2003/0023512 A1 | 1/2003 | Festa |
| 2003/0023513 A1 | 1/2003 | Festa |
| 2003/0033284 A1 | 2/2003 | Warren |
| 2003/0058267 A1 | 3/2003 | Warren |
| 2003/0061195 A1 | 3/2003 | Laborde |
| 2003/0072424 A1 | 4/2003 | Evans |
| 2003/0101165 A1 | 5/2003 | Warren |
| 2003/0105811 A1 | 6/2003 | Laborde |
| 2003/0107487 A1 | 6/2003 | Korman |
| 2003/0135403 A1 | 7/2003 | Sanderson |
| 2003/0154183 A1 | 8/2003 | Warren |
| 2003/0159030 A1 | 8/2003 | Evans |
| 2003/0163604 A1 | 8/2003 | Rabinovich |
| 2003/0163779 A1 | 8/2003 | Warren |
| 2003/0164857 A1 | 9/2003 | Warren |
| 2003/0178482 A1 | 9/2003 | Kisliakov |
| 2004/0002958 A1 | 1/2004 | Seshadri |
| 2004/0002988 A1 | 1/2004 | Seshadri |
| 2004/0019696 A1 | 1/2004 | Scott |
| 2004/0036715 A1 | 2/2004 | Warren |
| 2004/0036718 A1 | 2/2004 | Warren |
| 2004/0036722 A1 | 2/2004 | Warren |
| 2004/0039597 A1 | 2/2004 | Barts |
| 2004/0039989 A1 | 2/2004 | Warren |
| 2004/0044866 A1 | 3/2004 | Casazza |
| 2004/0054554 A1 | 3/2004 | Barts |
| 2004/0073127 A1 | 4/2004 | Istvan |
| 2004/0073448 A1 | 4/2004 | Barts |
| 2004/0083264 A1 | 4/2004 | Veselov |
| 2004/0107111 A1 | 6/2004 | Barts |
| 2004/0122827 A1 | 6/2004 | Cazemier |
| 2004/0127802 A1 | 7/2004 | Istvan |
| 2004/0133080 A1* | 7/2004 | Mazar .................... G06Q 50/22 600/300 |
| 2004/0139122 A1 | 7/2004 | Kanai |
| 2004/0139444 A1 | 7/2004 | Hope |
| 2004/0148304 A1 | 7/2004 | Hempstead |
| 2004/0210458 A1 | 10/2004 | Evans |
| 2005/0015355 A1 | 1/2005 | Heller |
| 2005/0015439 A1 | 1/2005 | Balaji |
| 2005/0080322 A1 | 4/2005 | Korman |
| 2005/0101843 A1 | 5/2005 | Quinn |
| 2005/0125742 A1 | 6/2005 | Grotjohn |
| 2005/0148882 A1 | 7/2005 | Banet |
| 2005/0149942 A1 | 7/2005 | Venkatraman |
| 2005/0204282 A1 | 9/2005 | Harutunian |
| 2005/0206518 A1* | 9/2005 | Welch .................... A61B 5/0024 340/539.12 |
| 2005/0216199 A1 | 9/2005 | Banet |
| 2005/0228244 A1 | 10/2005 | Banet |
| 2005/0228297 A1 | 10/2005 | Banet |
| 2005/0228299 A1 | 10/2005 | Banet |
| 2005/0245831 A1 | 11/2005 | Banet |
| 2005/0251002 A1 | 11/2005 | Istvan |
| 2005/0251003 A1 | 11/2005 | Istvan |
| 2005/0251004 A1 | 11/2005 | Istvan |
| 2005/0261594 A1 | 11/2005 | Banet |
| 2005/0261598 A1 | 11/2005 | Banet |
| 2005/0288986 A1 | 12/2005 | Barts |
| 2006/0009697 A1 | 1/2006 | Banet |
| 2006/0009698 A1 | 1/2006 | Banet |
| 2006/0031102 A1 | 2/2006 | Teller |
| 2006/0047215 A1 | 3/2006 | Newman |
| 2006/0047447 A1 | 3/2006 | Brady |
| 2006/0069319 A1 | 3/2006 | Elhag |
| 2006/0069702 A1 | 3/2006 | Moeller |
| 2006/0075251 A1 | 4/2006 | Correl |
| 2006/0079794 A1 | 4/2006 | Liu |
| 2006/0084878 A1 | 4/2006 | Banet |
| 2006/0117177 A1 | 6/2006 | Buer |
| 2006/0122474 A1 | 6/2006 | Teller |
| 2006/0122517 A1 | 6/2006 | Banet |
| 2006/0122520 A1 | 6/2006 | Banet |
| 2006/0142648 A1 | 6/2006 | Banet |
| 2006/0155589 A1 | 7/2006 | Lane |
| 2006/0161395 A1 | 7/2006 | Beam |
| 2006/0190931 A1 | 8/2006 | Scott |
| 2006/0218501 A1 | 9/2006 | Wilson |
| 2006/0224051 A1 | 10/2006 | Teller |
| 2006/0239215 A1 | 10/2006 | Munje |
| 2006/0241961 A1 | 10/2006 | Tsyganskiy |
| 2006/0241999 A1 | 10/2006 | Tsyganskiy |
| 2006/0242170 A1 | 10/2006 | Tsyganskiy |
| 2006/0242171 A1 | 10/2006 | Tsyganskiy |
| 2006/0242172 A1 | 10/2006 | Tsyganskiy |
| 2006/0242173 A1 | 10/2006 | Tsyganskiy |
| 2006/0242174 A1 | 10/2006 | Tsyganskiy |
| 2006/0242175 A1 | 10/2006 | Tsyganskiy |
| 2006/0242176 A1 | 10/2006 | Tsyganskiy |
| 2006/0242177 A1 | 10/2006 | Tsyganskiy |
| 2006/0242188 A1 | 10/2006 | Tsyganskiy |
| 2006/0242196 A1 | 10/2006 | Tsyganskiy |
| 2006/0242197 A1 | 10/2006 | Tsyganskiy |
| 2006/0242207 A1 | 10/2006 | Tsyganskiy |
| 2006/0264730 A1 | 11/2006 | Stivoric |
| 2006/0273878 A1 | 12/2006 | Michmerhuizen |
| 2006/0282401 A1 | 12/2006 | Waggoner |
| 2006/0282458 A1 | 12/2006 | Tsyganskiy |
| 2006/0293934 A1 | 12/2006 | Tsyganskiy |
| 2006/0293935 A1 | 12/2006 | Tsyganskiy |
| 2006/0293940 A1 | 12/2006 | Tsyganskiy |
| 2006/0294158 A1 | 12/2006 | Tsyganskiy |
| 2007/0011026 A1 | 1/2007 | Higgins |
| 2007/0011465 A1 | 1/2007 | Webber |
| 2007/0015973 A1 | 1/2007 | Nanikashvili |
| 2007/0015974 A1 | 1/2007 | Higgins |
| 2007/0038038 A1 | 2/2007 | Stivoric |
| 2007/0050395 A1 | 3/2007 | Hunter |
| 2007/0050404 A1 | 3/2007 | Hunter |
| 2007/0055166 A1 | 3/2007 | Patil |
| 2007/0067773 A1 | 3/2007 | Hope |
| 2007/0071643 A1 | 3/2007 | Hall |
| 2007/0073178 A1 | 3/2007 | Browning |
| 2007/0073558 A1 | 3/2007 | Hall |
| 2007/0116223 A1 | 5/2007 | Burke |
| 2007/0116224 A1 | 5/2007 | Burke |
| 2007/0118613 A1 | 5/2007 | Festa |
| 2007/0129958 A1 | 6/2007 | Wu |
| 2007/0129961 A1 | 6/2007 | Skibinski |
| 2007/0129962 A1 | 6/2007 | Skibinski |
| 2007/0129963 A1 | 6/2007 | Skibinski |
| 2007/0139219 A1* | 6/2007 | Crider .................... G01D 4/004 340/870.02 |
| 2007/0142715 A1 | 6/2007 | Banet |
| 2007/0168228 A1 | 7/2007 | Lawless |
| 2007/0169043 A1 | 7/2007 | Violleau |
| 2007/0180140 A1 | 8/2007 | Welch |
| 2007/0185393 A1 | 8/2007 | Zhou |
| 2007/0226196 A1 | 9/2007 | Adya |
| 2007/0226203 A1 | 9/2007 | Adya |
| 2007/0255122 A1 | 11/2007 | Vol |
| 2007/0276261 A1 | 11/2007 | Banet |
| 2007/0276262 A1 | 11/2007 | Banet |
| 2007/0276632 A1 | 11/2007 | Banet |
| 2007/0291834 A1 | 12/2007 | Toumazou |
| 2007/0293781 A1 | 12/2007 | Sims |
| 2007/0299854 A1 | 12/2007 | Bohlmann |
| 2008/0004538 A1 | 1/2008 | Virtanen |
| 2008/0009694 A1 | 1/2008 | Hopman |
| 2008/0013120 A1 | 1/2008 | Ying |
| 2008/0051670 A1 | 2/2008 | Banet |
| 2008/0058614 A1 | 3/2008 | Banet |
| 2008/0059877 A1 | 3/2008 | Brookler |
| 2008/0077026 A1 | 3/2008 | Banet |
| 2008/0082004 A1 | 4/2008 | Banet |

(56) References Cited

U.S. PATENT DOCUMENTS

| | | |
|---|---|---|
| 2008/0094228 A1 | 4/2008 | Welch |
| 2008/0097178 A1 | 4/2008 | Banet |
| 2008/0097550 A1 | 4/2008 | Dicks |
| 2008/0097551 A1 | 4/2008 | Dicks |
| 2008/0097552 A1 | 4/2008 | Dicks |
| 2008/0097793 A1 | 4/2008 | Dicks |
| 2008/0097908 A1 | 4/2008 | Dicks |
| 2008/0097909 A1 | 4/2008 | Dicks |
| 2008/0097910 A1 | 4/2008 | Dicks |
| 2008/0097911 A1 | 4/2008 | Dicks |
| 2008/0097912 A1 | 4/2008 | Dicks |
| 2008/0097913 A1 | 4/2008 | Dicks |
| 2008/0097914 A1 | 4/2008 | Dicks |
| 2008/0097917 A1 | 4/2008 | Dicks |
| 2008/0103370 A1 | 5/2008 | Dicks |
| 2008/0103405 A1 | 5/2008 | Banet |
| 2008/0103554 A1 | 5/2008 | Dicks |
| 2008/0103555 A1 | 5/2008 | Dicks |
| 2008/0114220 A1 | 5/2008 | Banet |
| 2008/0139953 A1 | 6/2008 | Baker |
| 2008/0150919 A1 | 6/2008 | Kanamaru |
| 2008/0183052 A1 | 7/2008 | Teller |
| 2008/0183502 A1 | 7/2008 | Dicks |
| 2008/0215120 A1 | 9/2008 | Dicks |
| 2008/0215360 A1 | 9/2008 | Dicks |
| 2008/0218376 A1 | 9/2008 | Dicks |
| 2008/0221399 A1 | 9/2008 | Zhou |
| 2008/0221461 A1 | 9/2008 | Zhou |
| 2008/0224852 A1 | 9/2008 | Dicks |
| 2008/0228697 A1 | 9/2008 | Adya |
| 2008/0281168 A1 | 11/2008 | Gibson |
| 2008/0282258 A1 | 11/2008 | Madej |
| 2008/0287751 A1 | 11/2008 | Stivoric |
| 2008/0287817 A1 | 11/2008 | Stivoric |
| 2008/0294020 A1 | 11/2008 | Sapounas |
| 2008/0300572 A1* | 12/2008 | Rankers ............ A61B 5/14532 604/504 |
| 2008/0306357 A1 | 12/2008 | Korman |
| 2008/0312542 A1 | 12/2008 | Banet |
| 2008/0319282 A1 | 12/2008 | Tran |
| 2008/0319327 A1 | 12/2008 | Banet |
| 2009/0018409 A1 | 1/2009 | Banet |
| 2009/0018422 A1 | 1/2009 | Banet |
| 2009/0018453 A1 | 1/2009 | Banet |
| 2009/0031340 A1 | 1/2009 | Modi |
| 2009/0054737 A1 | 2/2009 | Magar |
| 2009/0069642 A1 | 3/2009 | Gao et al. |
| 2009/0070412 A1 | 3/2009 | D'Angelo |
| 2009/0073991 A1 | 3/2009 | Landrum |
| 2009/0076340 A1 | 3/2009 | Libbus |
| 2009/0076341 A1 | 3/2009 | James |
| 2009/0076343 A1 | 3/2009 | James |
| 2009/0076344 A1 | 3/2009 | Libbus |
| 2009/0076345 A1 | 3/2009 | Manicka |
| 2009/0076349 A1 | 3/2009 | Libbus |
| 2009/0076350 A1 | 3/2009 | Bly |
| 2009/0076363 A1 | 3/2009 | Bly |
| 2009/0076397 A1 | 3/2009 | Libbus |
| 2009/0076401 A1 | 3/2009 | Mazar |
| 2009/0076405 A1 | 3/2009 | Amurthur |
| 2009/0076410 A1 | 3/2009 | Libbus |
| 2009/0076559 A1 | 3/2009 | Libbus |
| 2009/0089379 A1 | 4/2009 | Pegg |
| 2009/0093687 A1 | 4/2009 | Telfort |
| 2009/0094364 A1 | 4/2009 | Stevens |
| 2009/0099469 A1 | 4/2009 | Flores |
| 2009/0099824 A1 | 4/2009 | Falash |
| 2009/0102611 A1 | 4/2009 | Quinn |
| 2009/0109874 A1* | 4/2009 | Migault ............ H04L 29/12066 370/254 |
| 2009/0112072 A1 | 4/2009 | Banet |
| 2009/0112769 A1 | 4/2009 | Dicks |
| 2009/0118628 A1 | 5/2009 | Zhou |
| 2009/0131759 A1 | 5/2009 | Sims |
| 2009/0156946 A1 | 6/2009 | Lane |
| 2009/0172633 A1 | 7/2009 | Tsyganskiy |
| 2009/0177551 A1 | 7/2009 | Cue |
| 2009/0182860 A1 | 7/2009 | Hwang |
| 2009/0201636 A1 | 8/2009 | Doherty et al. |
| 2009/0234672 A1 | 9/2009 | Dicks |
| 2009/0234721 A1 | 9/2009 | Bigelow |
| 2009/0254601 A1 | 10/2009 | Moeller |
| 2009/0276792 A1 | 11/2009 | Berry |
| 2009/0319535 A1 | 12/2009 | Webber |
| 2009/0322763 A1 | 12/2009 | Bang et al. |
| 2009/0327230 A1 | 12/2009 | Levin |
| 2010/0016745 A1 | 1/2010 | Crump |
| 2010/0037240 A1 | 2/2010 | Launay |
| 2010/0042722 A1 | 2/2010 | Klissner |
| 2010/0052914 A1 | 3/2010 | Tsai |
| 2010/0058480 A1* | 3/2010 | Hedberg ............ A61B 5/6843 726/26 |
| 2010/0082646 A1 | 4/2010 | Meek |
| 2010/0088692 A1 | 4/2010 | Rathi |
| 2010/0128709 A1 | 5/2010 | Liu |
| 2010/0130875 A1 | 5/2010 | Banet |
| 2010/0153865 A1 | 6/2010 | Barnes |
| 2010/0160794 A1 | 6/2010 | Banet |
| 2010/0160795 A1 | 6/2010 | Banet |
| 2010/0160796 A1 | 6/2010 | Banet |
| 2010/0160797 A1 | 6/2010 | Banet |
| 2010/0160798 A1 | 6/2010 | Banet |
| 2010/0168536 A1 | 7/2010 | Banet |
| 2010/0168589 A1 | 7/2010 | Banet |
| 2010/0192221 A1 | 7/2010 | Waggoner |
| 2010/0324936 A1* | 12/2010 | Vishnubhatla ........ G06F 19/322 705/3 |
| 2011/0246123 A1 | 10/2011 | DelloStritto |
| 2012/0053423 A1* | 3/2012 | Kenalty ............ A61B 5/0015 600/300 |

FOREIGN PATENT DOCUMENTS

| | | |
|---|---|---|
| DE | 60016416 T2 | 5/2005 |
| DE | 60022603 T2 | 6/2006 |
| DE | 60301899 T2 | 7/2006 |
| DE | 102005039343 A1 | 2/2007 |
| DE | 60213297 T2 | 8/2007 |
| DE | 602004012051 T2 | 4/2009 |
| EP | 0996072 A1 | 4/2000 |
| EP | 1091295 A2 | 4/2001 |
| EP | 1431886 A2 | 6/2004 |
| EP | 1431886 A3 | 6/2005 |
| EP | 1718088 A1 | 11/2006 |
| EP | 1830263 A2 | 9/2007 |
| EP | 1091295 B1 | 5/2008 |
| EP | 1990978 A1 | 11/2008 |
| EP | 1941696 B1 | 2/2010 |
| FR | 2752469 A1 | 2/1998 |
| FR | 2752469 B1 | 5/2006 |
| GB | 2395579 A | 5/2004 |
| GB | 2395579 B | 12/2004 |
| KR | 1020090003748 | 1/2009 |
| WO | 2001097703 A2 | 12/2001 |
| WO | 2002015515 A2 | 2/2002 |
| WO | 2002084449 A2 | 10/2002 |
| WO | 2004066514 A1 | 8/2004 |
| WO | 2005010778 A1 | 2/2005 |
| WO | 2005057362 A2 | 6/2005 |
| WO | 2007024379 A2 | 3/2007 |
| WO | 2007024459 A1 | 3/2007 |
| WO | 2007050158 A1 | 5/2007 |
| WO | 2007050159 A1 | 5/2007 |
| WO | 2007062260 A2 | 5/2007 |
| WO | 2007062260 A3 | 5/2007 |
| WO | 2007084955 A2 | 7/2007 |
| WO | 2007112009 A1 | 10/2007 |
| WO | 2008128709 A1 | 10/2008 |
| WO | 2008154648 A1 | 12/2008 |
| WO | 2009042416 A1 | 4/2009 |
| WO | 2009084708 A1 | 7/2009 |
| WO | 2009155558 A1 | 12/2009 |

(56) References Cited

FOREIGN PATENT DOCUMENTS

OTHER PUBLICATIONS

Aframe Digital—Features; © 2010 Aframe Digital Inc.; webpage accessed via: http://www.aframedigital.com/features.html[Dec. 20, 2010 12:29:40 PM]; 1 page.
Alive Technologies—Products webpage; accessed via http://www.alivetec.com/products.htm[Dec. 20, 2010 1:08:22 PM]; 2 pages.
ApexPro Enterprise-wide telemetry; © 2008 General Electric Company; EMEA M1171526 Jan. 2009; Global version DOC0519991; 8 pages.
Bar-Or, Amir et al.; BioStream: A System Architecture for Real-Time Processing of Physiological Signals; Cambridge Research Laboratory; HP Laboratories Cambridge; HPL-2004-128; Aug. 2, 2004; © IEEE 2004; 8 pages.
BIOTRONIK—excellence for life; The New BIOTRONIK Home Monitoring®; © BIOTRONIK 2010; webpage accessed via: http://www.biotronik.com/en/us/25359[Dec. 20, 2010 12:58:45 PM]; 2 pages.
Card Guard Products & Technologies; accessed Mar. 4, 2011 via: http://www.cardguard.com/cardguard; 2 pages.
Cardiocom—Commander; Commander Data Management System; © 2010 Cardiocom, LLC; webpage accessed via: http://www.cardiocom.com/commander.html[Dec. 20, 2010 12:27:35 PM]; 2 pages.
CardioNet—Get to the Heart of the Problem; © CardioNet 2002-2010; webpage accessed via: http://www.cardionet.com/about_01.html[Dec. 20, 2010 12:32:35 PM]; 1 page.
CardioScout 24h ECG; SRM Innovative Medical Solutions; Web: www.sr-med.de; Copyright 2013 Alle Rechte vorbehalten; 2 pages.
CardioScout mobile; SRM Innovative Medical Solutions; © Urheberrechlich geschutzt; CS60011ASR-de; Web: www.sr-med.de; Copyright 2013 Alle Rechte vorbehalten; 2 pages.
CINTERION—Health Care; How can M2M improve your life.; webpage accessed via: http://cinterion.com/ehealth.htm[Dec. 20, 2010 12:39:09 PM]; 2 pages.
CodeBlue: Wireless Sensors for Medical Care; Harvard Sensor Networks Lab; accessed via http://fiji.eecs.harvard.edu/CodeBlue[Dec. 20, 2010 1:17:43 PM]; 4 pages.
Configurable Notification System IP Landscape; Blue Highway, LLC; Sep. 10, 2010.
Corscience—ECG Event recorder; corscience cardiovascular innovations; webpage accessed via: http://www.corscience.de/en/medical-engineering/products-systems/ecg-devices/event-recorder.html[Dec. 20, 2010 1:15:40 PM]; 2 pages.
Corventis™—Products; AVIVO™ Mobile Patient Management (MPM) System; © 2009 Corventis, Inc.; webpage accessed via: http://www.corventis.com/AP/avivo.asp[Dec. 20, 2010 12:37:49 PM]; 2 pages.
Crystal Monitor® PSG Series; PSG anywhere: Expanding the reach of your sleep services; Cleveland Medical Devices Inc.; LMA-07-0108 B; 2 pages; (admitted prior art as of the earliest priority date of this patent application).
Cybernet Medical®—How MedStar Works; webpage accessed via: http://www.cybernetmedical.com/index.php/how-medstar-works[Dec. 20, 2010 12:42:40 PM]; 1 page.
E-CliniQ—Tele Modem™ for Telephone Lines Connect-LAN™ for IP Networks Connect-CELL™ for Cellular Networks; Aerotel Medical Systems (1998) Ltd.; 2 pages.
FitLinxx: Activity and Health Tracking Technology; © 2008-2009 FitLinxx; webpage accessed via: http://fitlinxx.com/products_HW-pub.html[Dec. 20, 2010 12:43:27 PM]; 2 pages.
HealthSense—eNeighbor® System Components; Copyright Healthsense®; webpage accesses via: http://healthsense.com/index.php/products/eneighbor-system-components[Dec. 20, 2010 12:49:17 PM]; 5 pages.
HealthSense—eNeighbor® Typical Sensor Application; Copyright Healthsense®; webpage accessed via: http://healthsense.com/index.php/products/eneighbor-auto-pers-with-adl-monitoring/eneighbor-typical-sensor-application[Dec. 20, 2010 12:48:41 PM]; 1 page.
Healy, Jennifer et al.; Wearable Wellness Monitoring Using ECG and Accelerometer Data; Cambridge Research Laboratory; HP Laboratories Cambridge; HPL-2005-134; Jul. 13, 2005; © IEEE 2005; 4 pages.
Holst Centre: News & Press Releases; Best Paper Award for Micropower team during SSI2009; Mar. 12, 2009; accessed Feb. 21, 2011 via: http://www.holstcentre.com/NewsPress/NewsList/BestPaperAwardMicropower.aspx; 2 pages.
Holst Centre: News & Press Releases; Press Release: Body Area Network Monitors Arousal Level; Oct. 14, 2008; accessed Feb. 21, 2011 via: http://www.holstcentre.com/NewsPress/PressList/Body%20area%20network%20monitors%20arousal%20level.aspx; 2 pages.
Honeywell HomMed; Genesis Features; © Honeywell International Inc. 2007; webpage accessed via: http://www.hommed.com/products/genesis_features.asp[Dec. 20, 2010 1:19:56 PM]; 1 page.
Honeywell HomMed; Sentry Telehealth Monitor—Total Solution; © Honeywell International Inc. 2007; webpage accessed via: http://www.hommed.com/products/sentry_telehealth_monitor-total-solution.asp[Dec. 20, 2010 1:21:06 PM]; 1 page.
Honeywell: Honeywell HomMed—Features; © Honeywell International Inc. 2007; accessed Feb. 21, 2011 via: http://www.hommed.com/products/genesis_features.asp; 1 page.
http://ieeexplore.ieee.org/stampPDF/getPDF.jsp?arnumber=1385537&isnumber=30166 Integration Technology Adoption in Healthcare Organizations: A Case for Enterprise Application Integration; System Sciences, 2005.
http://ieeexplore.ieee.org/stampPDF/getPDF.jsp?arnumber=1400944&isnumber=30424 Network middleware for flexible integration of sensor processing in home environment; Systems, Man and Cybernetics, 2004 IEEE International Conference.
http://ieeexplore.ieee.org/stampPDF/getPDF.jsp?arnumber=1503146&isnumber=32244 Distributed automatic camera control system tracking markers for distance education; Information Technology: Research and Education, 2005.
http://ieeexplore.ieee.org/stampPDF/getPDF.jsp?arnumber=1557107&isnumber=33064 Acquiring medium models for sensing performance estimation; Sensor and Ad Hoc Communications and Networks, 2005.
http://ieeexplore.ieee.org/stampPDF/getPDF.jsp?arnumber=1585716&isnumber=33446 The Relational Data Model for Design Automation; Design Automation, 1983.
http://ieeexplore.ieee.org/stampPDF/getPDF.jsp?arnumber=1634230&isnumber=34262 Network ready CBRN sensors: a way forward; Sensors Applications Symposium, 2006.
http://ieeexplore.ieee.org/stampPDF/getPDF.jsp?arnumber=1653976&isnumber=34667 New Products; Mar. 1982; 6 pages.
http://ieeexplore.ieee.org/stampPDF/getPDF.jsp?arnumber=275682&isnumber=6831 The case for application-specific operating systems; Workstation Operating Systems, 1992. Proceedings.
http://ieeexplore.ieee.org/stampPDF/getPDF.jsp?arnumber=4746473&isnumber=4746420 Intelligent Enterprise Information Security Architecture Based on Service Oriented Architecture; Future Information Technology and Management Engineering, 2008.
http://ieeexplore.ieee.org/stampPDF/getPDF.jsp?arnumber=4810140&isnumber=4814874 Modeling the Ambient Intelligence Application System: Concept, Software, Data, and Network; Systems, Man, and Cybernetics, Part C: Applications and Reviews, IEEE Transactions on pp. 299-314, Apr. 3, 2009.
http://ieeexplore.ieee.org/stampPDF/getPDF.jsp?arnumber=486713&isnumber=10418 Evolution of virtual reality [Medicine]; Engineering in Medicine and Biology Magazine, IEEE (vol. 15, Issue: 2), Mar./Apr. 1996.
http://ieeexplore.ieee.org/stampPDF/getPDF.jsp?arnumber=5159015&isnumber=5158914 Increasing Overall Network Security by Integrating Signature-Based NIDS with Packet Filtering Firewall; Artificial Intelligence, 2009.

(56) References Cited

OTHER PUBLICATIONS http://ieeexplore.ieee.org/stampPDF/getPDF.jsp?arnumber=5337255&isnumber=5337084 Web 3.0: A Real Personal Web! More Opportunities and More Threats; Next Generation Mobile Applications, Services and Technologies, 2009.
http://ieeexplore.ieee.org/stampPDF/getPDF.jsp?arnumber=5451719&isnumber=5451538 Development on object-oriented virtual assembly system for series products; Computer and Automation Engineering (ICCAE), Feb. 2010 (vol. 4).
http://ieeexplore.ieee.org/stampPDF/getPDF.jsp?arnumber=651147&isnumber=14154 Beyond calculation: the expanded use of computer-generated transformer design data; Electrical Insulation Conference, 1997, and Electrical Manufacturing Coil Winding Conference.
http://ieeexplore.ieee.org/stampPDF/getPDF.jsp?arnumber=765767&isnumber=16540 Multiple dynamic view support for cooperative work; Database Systems for Advanced Applications, 1999.
http://ieeexplore.ieee.org/stampPDF/getPDF.jsp?arnumber=864027&isnumber=18717 An implementation of a CSCW framework using CORBA; High-Performance Communication Systems, 1997.
http://ieeexplore.ieee.org/stampPDF/getPDF.jsp?arnumber=885633&isnumber=19092 Combining the "information" and "measurement" worlds to improve system performance and operational readiness; AUTOTESTCON Proceedings, 2000 IEEE.
http://ieeexplore.ieee.org/stampPDF/getPDF.jsp?arnumber=928623&isnumber=20074 XML's impact an databases and data sharing; Computer (vol. 34, Issue: 6) Jun. 2001.
http://ieeexplore.ieee.org/stampPDF/getPDF.jsp?arnumber=935390&isnumber=20240 Traffic shaping in end systems attached to QoS-supporting networks; Computers and Communications, 2001.
http://ieeexplore.ieee.org/stampPDF/getPDF.jsp?arnumber=948854&isnumber=20512 Optimal resource assignment in Internet data centers; Modeling, Analysis and Simulation of Computer and Telecommunication Systems, 2001.
http://ieeexplore.ieee.org/stampPDF/getPDF.jsp?arnumber=952440&isnumber=20588 GEODAS: an industrial experience with component frameworks for data acquisition and analysis systems; Euromicro Conference, 2001. Proceedings. $27^{th}$.
http://ieeexplore.ieee.org/stampPDF/getPDF.jsp?arnumber=965924&isnumber=20834 An XML-based architecture for distributed real-time multimedia systems; Global Telecommunications Conference, 2001. GLOBECOM '01. IEEE (vol. 3).
http://ieeexplore.ieee.org/stampPDF/getPDF.jsp?arnumber=994528&isnumber=21442 P2P in B2BI; System Sciences, 2002. HICSS.
http://sourceforge.net/projects/nors/—pdf of page accessed Feb. 21, 2011; 2 pages.
http://wiki.forum.nokia.com/index.php/Nokia_Open_Source—pdf of page accessed Feb. 21, 2011; 2 pages.
http://www.corventis.com/AP/avivo.asp—pdf of page accessed Feb. 21, 2011; 2 pages.
http://www.corventis.com/US/—pdf of page accessed Feb. 21, 2011; 1 page.
http://www.eecs.harvard.edut~mdw/proj/codeblue/release—pdf of page accessed Feb. 21, 2011; 2 pages.
http://www.holstcentre.com/—pdf of page accessed Aug. 1, 2011; 1 page.
http://www.picomed.de/—pdf of page accessed Mar. 4, 2011; 1 page.
http://www.shimmer-research.com/—pdf of page accessed Feb. 21, 2011; 1 page.
http://www.spauldingrehab.org/—pdf of page accessed Feb. 21, 2011; 1 page.
http://www2.imec.be/imec_com/imec_com_homepage.php—pdf of page accessed Feb. 21, 2011; 2 pages.
Ideal Life—Products; © IDEAL LIFE®; webpage accessed via: http://ideallifeonline.com/products/[Dec. 20, 2010 12:34:02 PM]; 2 pages.
Imec—Human ++: body area networks; Scientific Report 2008; webpage accessed via: http://www.imec.be/ScientificReport/SR2008/HTML/1225020.html[Dec. 20, 2010 1:30:57 PM]; 4 pages.
Imec—Integrated wearable systems; Scientific Report 2009; webpage accessed via: http://www.imec.be/ScientificReport/SR2009/HTML/1213373.html[Dec. 20, 2010 1:26:38 PM]; 6 pages.
Instromedix—Cardiac Event Recorders & Pacemaker Checks; LifeStar HealtheKit—Vital Signs Monitoring; © 2004 Card Group® Group of Companies; webpage accessed via: http://www.instromedix.com/HealtheKit.htm[Dec. 20, 2010 2:20:28 PM]; 2 pages.
Intel® Health Guide PHS6000—Connecting patients and healthcare professionals for personalized care—Product Brief; © 2009 Intel Corporation; 4 pages.
Intel in Healthcare—homepage; accessed Feb. 21, 2011 via: http://www.intel.com/about/companyinfo/healthcare/index.htm; 2 pages.
Intelesens Responsive Healthcare—Vitalsens Wireless Platform; Product and Graphic Design by The Design Factor, Belfast; 4 pages; (admitted prior art as of the earliest priority date of this patent application).
Intel-GE Care Innovations—Intel Health Guide; The Next Step in Chronic Care Management: Personalized Health Monitoring at Home; © 2011 Intel-GE Care Innovations, LLC; accessed Feb. 21, 2011 via: http://www.careinnovations.com/products/healthguide/default.aspx; 1 page.
LifeSync Corporation; Wireless ECG and Wireless EKG; Hospital Infection Control; The New Standard in Monitoring Patients; © 2003-2008 LifeSync Corporation; V.1 Last Updated Jan. 6, 2009; webpage accessed via: http://www.lifesynccorp.com/products/wireless-system.html[Dec. 20, 2010 2:28:29 PM]; 7 pages.
Low-Power and Secure Wearable ECG over Body Area Network: Press Release; May 11, 2009; © 2008 National Institute of Information and Communications Technology; webpage accessed via: http://www2.nict.go.jp/pub/whatsnew/press/h21/090511/090511_e.html[Dec. 20, 2010 2:29:13 PM]; 5 pages.
MedApps® Mobile Health Monitoring; MedApps, Inc. © 2010; webpage accessed via: http://www.medapps.net/System.html[Dec. 20, 2010 12:13:57 PM]; 1 page.
Medical News Today; Sensei and Humana Inc. Join Forces to Offer Humana Associates Innovative Program for Weight Loss; Jan. 30, 2008; accessed via: http://www.medicalnewstoday.com/articles/95560.php[Dec. 20, 2010 4:34:59 PM]; 4 pages.
MediCompass Integrated Product Suite; MediCompass Product Suite—IDNs; P/N: 70/9564 Rev A; Copyright © 1999-2010 iMetrikus®, Inc.; 2 pages.
MetriLink®; MetriLink P/N: 70/9571 Rev A; Copyright © 1999-2010 iMetrikus®, Inc.; 2 pages.
Mindray—NetGuard™—Features & Benefits; © 2010 Mindray DS USA, Inc.; webpage accessed via: http://www.mindray.com/na/products/netguard.html?backUrl=http://www.mindray.com/na/products/pro_line1_pre.html[1 Feb. 20, 2010 12:55:12 PM]; 2 pages.
Mobile Health Zone—Sensei Corp; Copyright © 2010 Sensei Corp.; accessed via: http://www.sensei.com/mobile-health-zone/[Dec. 20, 2010 4:33:53 PM]; 1 page.
Nee, O. et al.; SAPHIRE: intelligent healthcare monitoring based on semantic interoperability platform: pilot applications; IET Commun., Feb. 2008, vol. 2, No. 2, pp. 192-201; © The Institution of Engineering and Technology 2008; 10 pages.
New Wireless Devices Could Help Consumers Keep Track of their Vital Signs; San Diego, CA, Dec. 20, 2007; Calit2: California Institute for Telecommunications and Information Technology; accessed via: Http://www.calit2.net/newsroom/print_page.php?id=1211[Dec. 20, 2010 4:05:27 PM]; 3 pages.
Personal Health Monitor—Features; © 2005-2010 University of Technology, Sydney; webpage accessed via: http://personalheartmonitor.com/Features.html[Dec. 20, 2010 3:31:49 PM]; 3 pages.
Personal Health Monitor—Welcome; © 2005-2010 University of Technology, Sydney; webpage accessed via: http://personalheartmonitor.com/index.html[Dec. 20, 2010 3:30:57 PM]; 2 pages.
Personal Health Monitor; Mar. 2010 Version 4.2.8 Released; © 2005-2010 University of Technology, Sydney; accessed Mar. 3, 2011 via: http://personalheartmonitor.com/news.html; 3 pages.

(56) References Cited

OTHER PUBLICATIONS

Planet Automation.com: Eaton Chooses Intrinsyc for Embedded WinCE Solution; Jul. 20, 2000; © 1996-2001 VertMarkets, Inc.; accessed Aug. 9, 2011 via: http://www.plantautomation.com/article.mvc/Eaton-chooses-Intrinsyc-for-embedded-WinCE-so-0001; 3 pages.
Pulse Oximetry/Fingertip; 9560 Onyx II—Product Literature; © 2008 Nonin Medical, Inc.; 4 pages.
Qualcomm Innovation—LifeCOMM; Innovation stories: The baby boomer wave; LifeCOMM and the "disease care" system; Closing the "continuum of care" gap; Innovation. Execution. Credibility; © 2010 Qualcomm Incorporated; accessed via: http://www.qualcomm.com.au/innovation/stories/lifecomm.html[Dec. 20, 2010 4:01:30 PM]; 2 pages.
Redengine Inc: Health Sector Clients: WWPM; Case Studies; accessed via: http://www.redengine.com/case-studies/health/wwpm.aspx[Dec. 20, 2010 4:11:48 PM]; 1 page.
SAPHIRE, "Intelligent Healthcare Monitoring based on a Semantic Interoperability Platform", Survey of the State of the Art, Feb. 28, 2006, pp. 192-201.
SenseWear—Product Overview; Introducing the Enhanced BodyMedia SenseWear System; webpage accessed via: http://sensewear.bodymedia.com/SW-Learn-More/Product-Overview[Dec. 20, 2010 1:12:29 PM]; 2 pages.
Sensium Life Pebble Wireless Vitals Monitor for Sport Training, Cardiac Health Auditing; medGadget internet journal of emerging medical technologies; Monday, Oct. 26, 2009; © 2004-2010 Medgadget LLC; webpage accessed via: http://medgadget.com/archives/2009/10/sensium_life_pebble_wireless_vitals_monitor_for_sport_training_cardiac_health_auditing.html[Dec. 20, 2010 2:58:27 PM]; 5 pages.
Sensor and modules; Shimmer: Discovery in Motion; © SHIMMER RESEARCH™; webpage accessed via: http://www.shimmer-research.com/p/sensor-and-modules[Dec. 20, 2010 2:54:06 PM]; 3 pages.
Shimmer Wireless Sensor Unit/Platform; Shimmer: Discovery in Motion; © SHIMMER RESEARCH™; webpage accessed via: http://www.shimmer-research.com/p/products/sensor-units-and-modules/shimmer-wireless-sensor-unitplatform[Dec. 20, 2010 2:54:59 PM]; 2 pages.
SleepScout™ Portable Sleep Monitor: Simplify the Monitoring of Sleep Disorders; Cleveland Medical Devices Inc.; LMA-08-0011 A Lab; 2 pages; (admitted prior art as of the earliest priority date of this patent application).
Sleuth AT Transoma's New Implantable Wireless ECG Monitor Gets US OK; Friday, Feb. 13, 2009; © 2004-2010 Medgadget LLC; accessed via: http://medgadget.com/archives/2009/02/transomas_new_implantable_wireless_ecg_monitor_gets_us_ok.html[Dec. 20, 2010 3:58:08 PM]; 5 pages.
Sleuth™ Wireless Electrocardiogram Monitoring System; Thursday, Oct. 18, 2007; © 2004-2010 Medgadget LLC; accessed via: http://medgadget.com/archives/2007/10/sleuth_wireless_electrocardiogram_monitoring_system.html[Dec. 20, 2010 3:58:43 PM]; 5 pages.
Sotera Wireless—Rapid Response Monitoring: A New Era in Ambulartory Patient Safety; © 2009 Sotera Wireless Inc., Formerly Triage Wireless; webpage accessed via: http://www.soterawireless.com/main/index.php?option=com_content&view=article&id=55&Itemid=18[Dec. 20, 2010 12:56:39 PM]; 1 page.
Sotera Wireless—Rapid Response Monitoring: Sotera Wireless Expands Management Team in Anticipation of Product Scale-Up in 2009; Jan. 12, 2009; © 2009 Sotera Wireless Inc. Formerly Triage Wireless; accessed Mar. 3, 2011 via: http://www.soterawireless.com/main/index.php?option=com_content&view=article&id=76:press-release-january09&catid=36:press-releases&Itemid=60; 2 pages.
Sotera Wireless—Rapid Response Monitoring: Union Tribune Sep. 2008; © 2009 Sotera Wireless Inc. Formerly Triage Wireless; accessed Mar. 3, 2011 via: http://www.soterawireless.com/main/index.php?option=com_content&view=article&id=50:union-tribune09-2008&catid=35:media-coverage&Itemid=29; 1 page.
Sudano, Isabella et al.; Auricall®. A new device for a non-invasive, wireless, continuous monitoring of oxygen saturation and heart rate in patients with heart failure; International Journal of Cardiology 129 (2008); pp. 141-143.
Thorn, C.F. et al.: Pathway-based Approaches to Pharmacogenomics; Current Pharmacogenomics, vol. 5, No. 1; © 2007 Bentham Science Publishers Ltd.; accessed Aug. 9, 2011 via: http://www.bentham.org/cppm/Sample/cpg5-1/007AF.pdf; pp. 79-86.
Toumaz—Pioneer in Low Cost, Ultra-Low Power Wireless Technologies; © 2011 Toumaz UK Ltd; accessed Mar. 4, 2011 via: http://www.toumaz.com/; 1 page.
Toumaz—Sensium Introduction: Sensium Ultra-Low Power Platform for Rapid Development of Wireless Body Area Networks (BANs); © 2010 Toumaz UK Ltd.; webpage accessed via: Http://www.toumaz.com/page.php?page=sensium_intro[Dec. 20, 2010 12:35:33 PM]; 2 pages.
UC-321 Precision Personal Health Scale—A&D Weighing Pty Ltd; © 2005 A&D Weighing Pty Ltd; accessed Mar. 3, 2011 via: http://www.andmercury.com.au/web.php?p=1305&pp=1390&pcat=scale; 1 page.
Welcome to Carematix.com—Carematix Wellness System; © 2002 Carematix Inc.; webpage accessed via: http://carematix.com/[Dec. 20, 2010 1:00:40 PM]; 1 page.
International Searching Authority, International Search Report and Written Opinion, PCT/US2011/055709, dated May 1, 2012, 11 pages.
Nicky Kern et al., "Multi-sensor Activity Context Detection for Wearable Computing," EUSAI 2003, pp. 220-232.

* cited by examiner

530

Application Privacy

┌─ BreathingMonitor ─────────┐
│ SMS privacy      ☐         │
│ Email privacy    ☑         │
│ Feed privacy     ☑         │
│ [Submit]                    │
└─────────────────────────────┘

┌─ Pain ──────────────────────┐
│ SMS privacy      ☐         │
│ Email privacy    ☑         │
│ Feed privacy     ☑         │
│ [Submit]                    │
└─────────────────────────────┘

┌─ WeightMonitor ─────────────┐
│ SMS privacy      ☐         │
│ Email privacy    ☑         │
│ Feed privacy     ☑         │
│ [Submit]                    │
└─────────────────────────────┘

┌─ SPO2 ──────────────────────┐
│ SMS privacy      ☐         │
│ Email privacy    ☑         │
│ Feed privacy     ☑         │
│ [Submit]                    │
└─────────────────────────────┘

┌─ Pedometer ─────────────────┐
│ SMS privacy      ☐         │
│ Email privacy    ☑         │
│ Feed privacy     ☑         │
│ [Submit]                    │
└─────────────────────────────┘

FIG. 17

PLATFORM FOR PATIENT MONITORING

CROSS REFERENCE TO RELATED APPLICATION(S)

This application is a divisional application of pending U.S. patent application Ser. No. 12/907,873, filed Oct. 19, 2010, the entirety of which is hereby incorporated by reference.

STATEMENT REGARDING FEDERALLY FUNDED RESEARCH OR DEVELOPMENT

These inventions were made with government support under Contract Nos. W81XWH-10-C-0159 and W81XWH-07-01-608 awarded by the United States Army Medical Research Acquisition Activity. The government may have certain rights in these inventions.

BACKGROUND

Healthcare practitioners can be constrained by the inability of devices used to monitor and collect physiological data from patients to communicate with electronic health records, existing infrastructure, and other devices. The medical device research community has responded by creating next generation devices that are small, wireless, and wearable. New devices may incorporate a display, processor, and multitude of companion sensors. There are one or more problems associated with patient monitoring devices that interface between wearable sensors and a network and/or external computing device. Such problems can include size, simplicity of operation, interface connectivity, and power supplies, among others.

SUMMARY

In one aspect, a gateway device includes a transceiver in electrical communication with a processor, the transceiver being configured to communicate over a wireless network to both receive data from at least one body-worn sensor and transmit the data, and a plurality of indicator lights in electrical communication with the processor. A first of the indicator lights indicates successful power-on of the gateway device. A second of the indicator lights indicates establishment of a Bluetooth connection with a body-worn sensor. A third of the indicator lights indicates successful creation of a WiFi connection. A fourth of the indicator lights indicate successful creation of a cellular connection.

In another aspect, a system for storing data collected by a body-worn sensor includes: a central processing unit (CPU) that is configured to control operation of a gateway device; and one or more computer readable data storage media storing software instructions that, when executed by the CPU, cause the gateway device to: receive a MAC address of a new sensor and a protocol version associated with the new sensor from a server; attempt to contact the new sensor using the protocol version and the MAC address; when a response is received, sending the response to the server for validation; when the response is validated by the server, establishing communications with the new sensor; and forwarding data from the new sensor to a second server.

In yet another aspect, a method for storing data from one or more body-worn sensors includes: receiving data from a gateway device, the gateway device being worn by a user associated with one or more body-worn sensors generating the data; identifying the user associated with the data; allowing a super application associated with the user to identify a database for storage of the data based on the user and a type of body-worn sensor that generated the data; and forwarding the data to the database for storage.

DESCRIPTION OF THE FIGURES

FIG. 17 shows another example user interface for accessing data associated with the system of FIG. 1.

DETAILED DESCRIPTION

The present disclosure relates to systems and methods that allow data from a plurality of sensor devices to be collected, processed, and displayed.

One embodiment includes a computer platform including a gateway device which wirelessly communicates with body-worn sensors. The gateway can be positioned on the patient or be located adjacent to the patient. The gateway device receives data from the body-worn sensors and communicates the data to a central server.

The example gateway device can include a power source, a transceiver in electrical communication with the processor, the transceiver being configured to communicate over a wireless network to both receive data from at least one sensor and transmit data, a plurality of indicator lights in electrical communication with the processor, and data storage including program instructions that, when executed by the processor, cause the gateway device to signal at least one of the plurality of indicator lights upon successful transmission of the data by the transceiver.

In one example, the gateway device includes a communications unit with one or more radios, including an uplink radio and a downlink radio, wherein the downlink, short range radio is configured to communicate with physiological sensors such as wireless wearable sensors to acquire data based on such protocols as Bluetooth or Zigbee, and the uplink radio is configured to wirelessly transmit data to a network based on such protocols as WiFi, 3G, and/or 4G. In another embodiment, the downlink and uplink radio maybe the same hardware multiplexing to service the downlink and uplink channels.

The gateway device can include on-board memory (such as SD card) configured to store data, such as patient medical history, to be used in emergencies or other data captured through the downlink, including data unable to complete the path to the network because of temporary uplink inaccessibility. The data storage can be further configured to store an operating system (e.g., Linux with Python support) and associated software to operate and control transmission of data, as well as employ various power saving techniques to increase battery life of the device for prolonged use.

Figure 1:
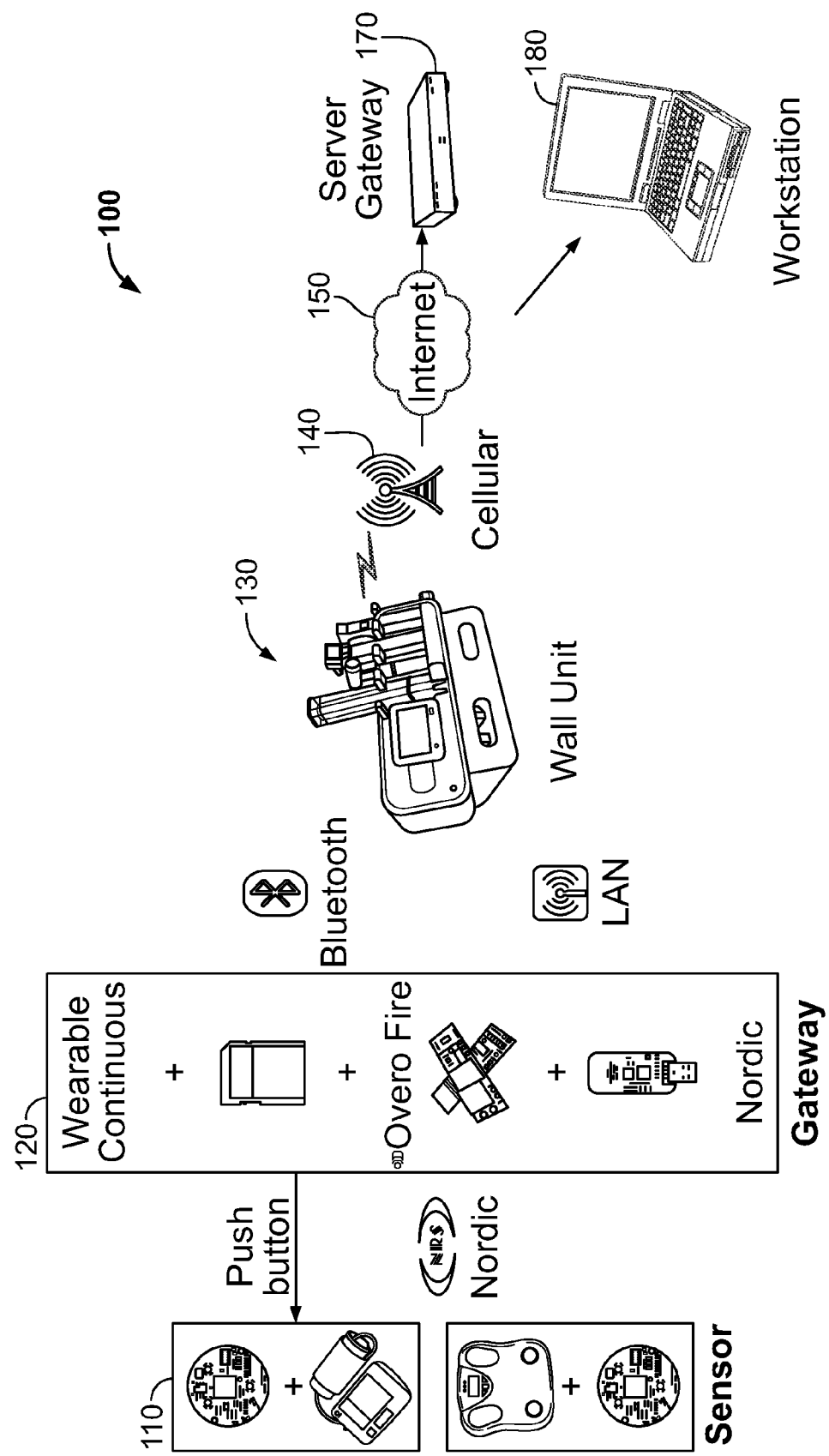
FIG. 1 shows an example system for collecting data associated with physiological parameters of patients.

Referring now to FIG. 1, a block diagram illustrates an example system 100 for collecting, processing, and displaying physiological data. In this example, the system 100 includes a plurality of sensor devices 110, a gateway device 120, a wall unit 130, networks 140, 150, a server 170, and a computing device 180.

The networks 140, 150 can be one or more electronic communication networks that facilitate communication between the sensor devices 110 and the gateway device 120 and the server 170. The networks 140, 150 can include a set of computing devices and links between the computing devices. The computing devices in the networks 140, 150 use the links to enable communication among the computing devices in the network.

The networks 140, 150 can include routers, switches, mobile access points, bridges, hubs, storage devices, stand-alone server devices, blade server devices, sensors, desktop computers, firewall devices, laptop computers, handheld computers, mobile telephones, and other types of computing devices. In various embodiments, the networks 140, 150 include various types of links. For example, the networks 140, 150 can include wired and/or wireless links. The networks 140, 150 can be implemented as one or more local area networks (LANs), metropolitan area networks, subnets, wide area networks (such as the Internet), or can be implemented at another scale.

In the example shown, the network 140 is a cellular network, and the network 150 is the Internet. Other configurations are possible.

The gateway device 120 is a computing system that allows for storage and forwarding of data collected by one or more of the sensor devices 110. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

Figure 2:
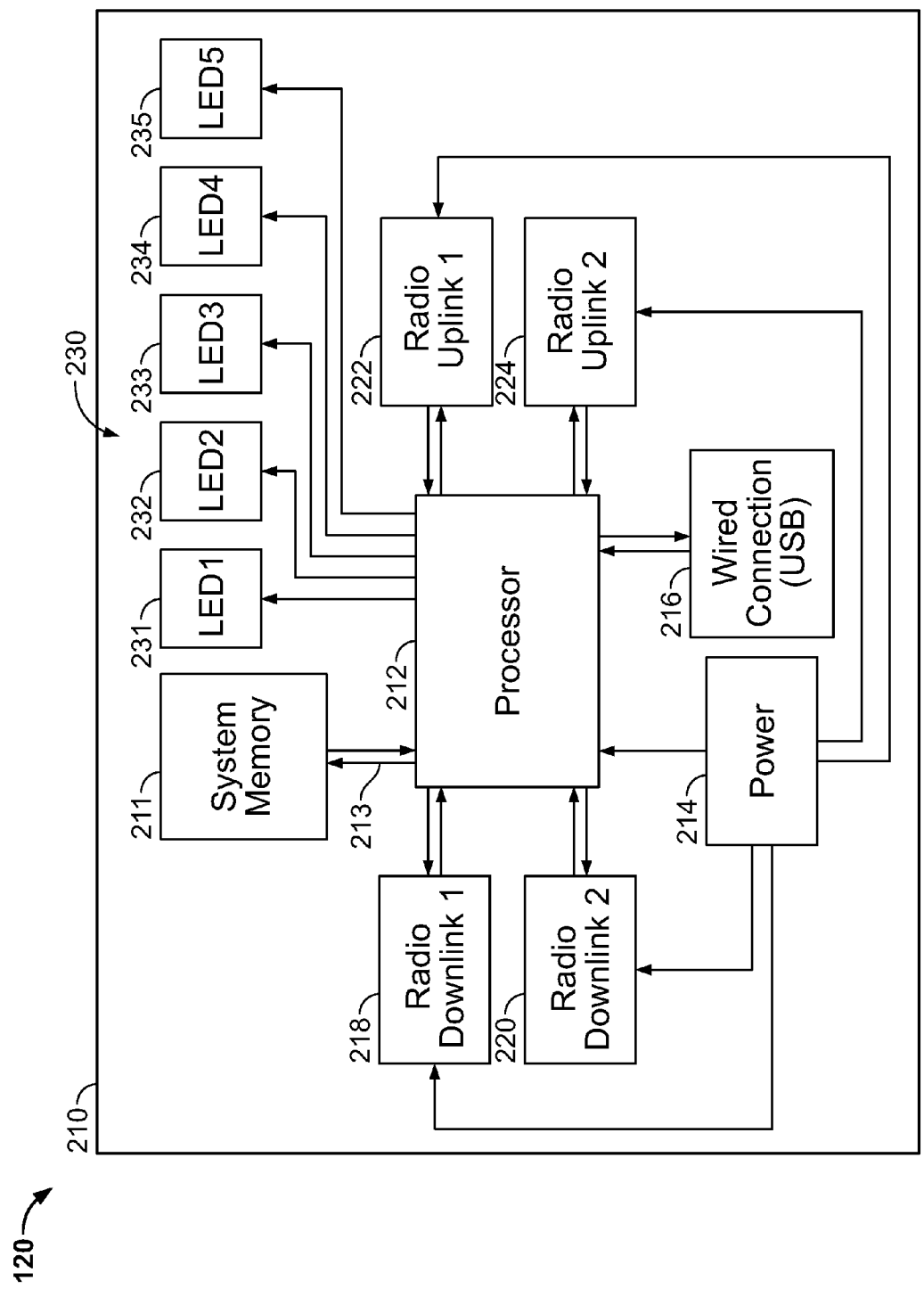
FIG. 2 shows an example schematic view of a gateway device of the system of FIG. 1.
Figure 3:
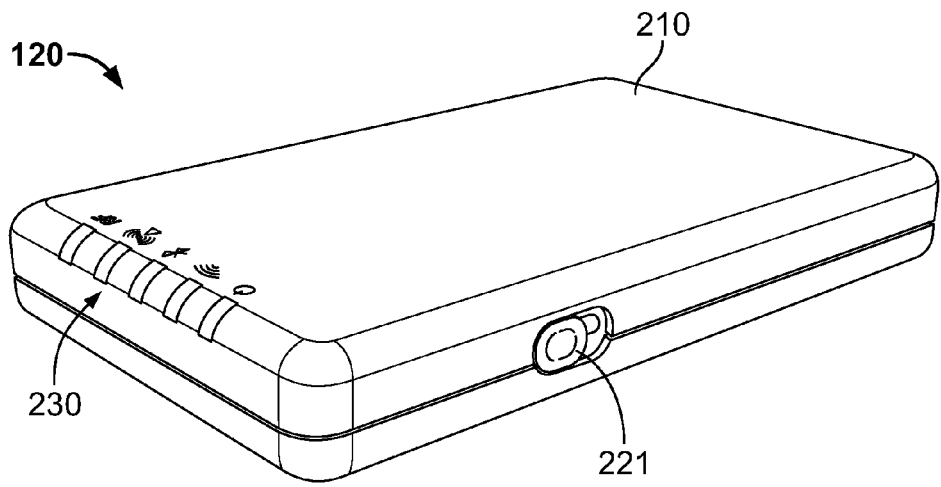
FIG. 3 shows a view of the gateway device of FIG. 1.
Figure 4:
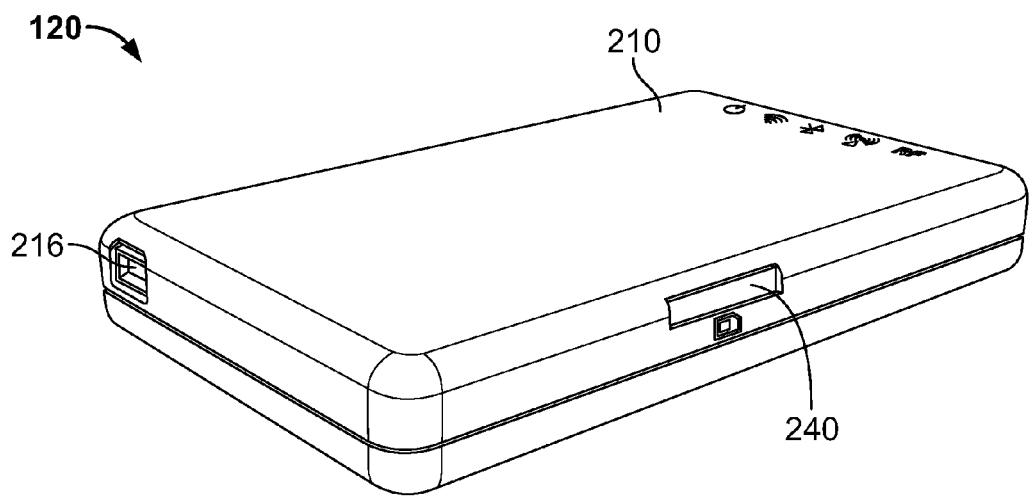
FIG. 4 shows another view of the gateway device of FIG. 3.
Figure 5:
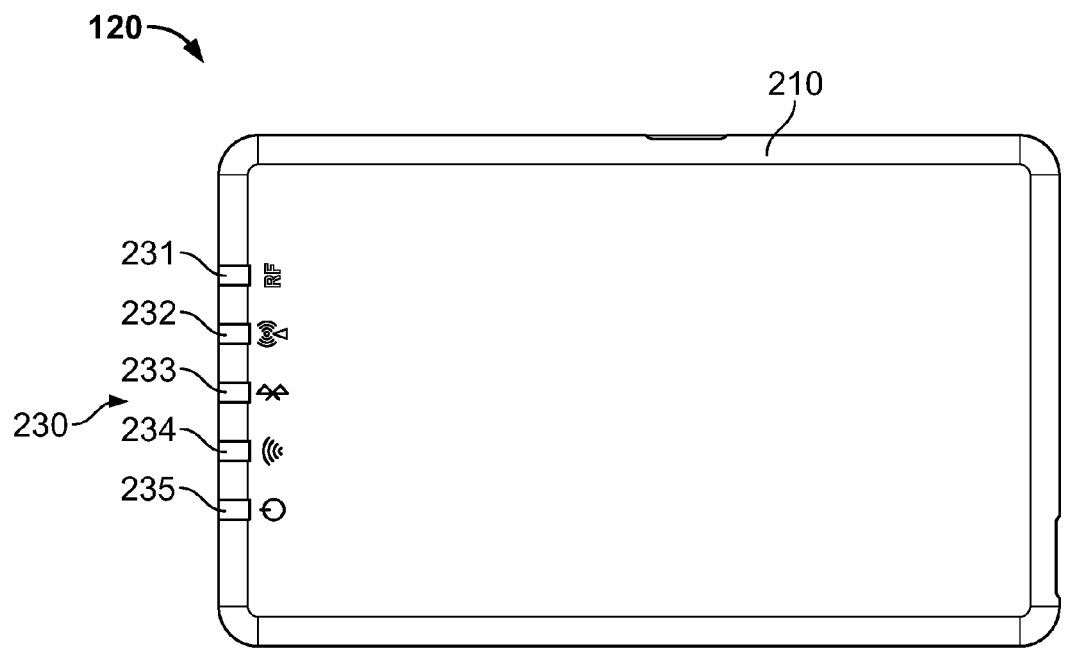
FIG. 5 shows another view of the gateway device of FIG. 3.
Figure 6:
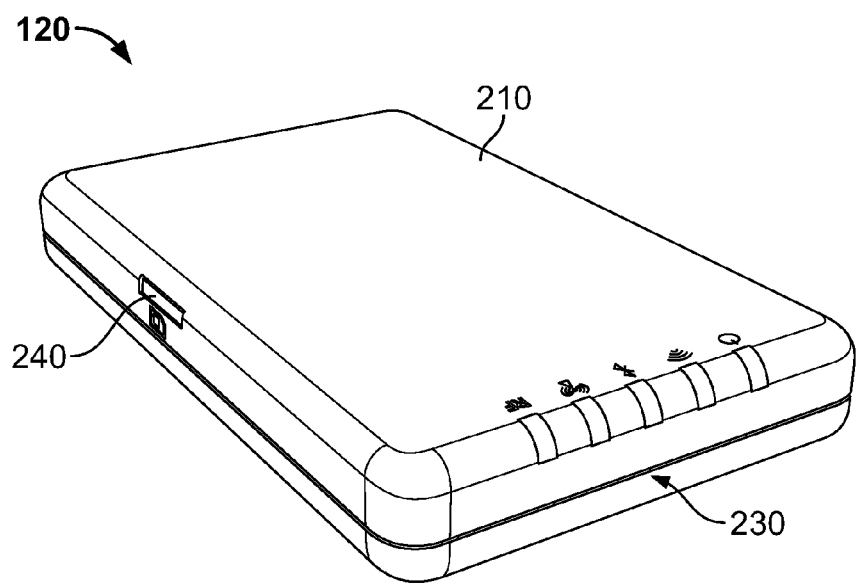
FIG. 6 shows another view of the gateway device of FIG. 3.

As shown in FIG. 2, the gateway device 120 can include at least one central processing unit ("CPU" or "processor") 212, a system memory 211, and a system bus 213 that couples the system memory 211 to the CPU 212.

In one example, the CPU 212 is a 266 MHz ARM926EJ-S core (16 KB I-Cache, 16 KB D-Cache) processor. The CPU 212 consumes approximately 1.8 volts and includes 32 MB Flash and 64 MB SDRAM onboard. Other configurations are possible.

The system memory 211 is one or more physical devices that can include a random access memory ("RAM") and a read-only memory ("ROM"). A basic input/output system containing the basic routines that help to transfer information between elements within the gateway device 120, such as during startup, is stored in the ROM. The system memory 211 of the gateway device 120 further includes a mass storage device. The mass storage device is able to store software instructions and data.

The mass storage device and its associated computer-readable data storage media provide non-volatile, non-transitory storage for the gateway device 120. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the gateway device 120 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the gateway device 120.

The system memory 211 of the gateway device 120 can store software instructions and data. The software instructions include an operating system suitable for controlling the operation of the gateway device 120. The system memory 211 also stores software instructions, that when executed by the CPU 212, cause the gateway device 120 to provide the functionality of the gateway device 120 discussed herein.

For example, the mass storage device and/or the RAM can store software instructions that, when executed by the CPU 212, cause the gateway device 120 to store and forward data that is provided by the sensor devices 110.

As noted previously, the gateway device 120 can operate in a networked environment using logical connections to remote network devices through the networks 140, 150, such as a local network, the Internet, or another type of network. The gateway device 120 connects to the networks 140, 150 through a network interface unit, such as the radio uplinks 222, 224 and the radio downlinks 218, 220.

In one example, the gateway device 120 communicates using GSM, including one or more of: HSDPA 7.2 Mbps, UMTS/HSDPA 2100 MHz, Quad-band EGSM 850/900/1800/1900, GPRS multi-slot class 12, and EDGE multi-slot class 12. The gateway device 120 also communicates through WiFi, using 802.11b/g with data rates up to 54 Mbps, IEEE 802.11i encryption, 64/128-bit WEP, TKIP and AES, WPA and WPA2 security. The gateway device 120 also communicates through Bluetooth using Bluetooth v2.1+ EDR compliant, CSR BlueCore 6 ROM, 2.40-2.480 GHz FHSS Radio, Max Data Rate 3 Mbps, Bluetooth Co-existence Support with 802.11. The gateway device 120 also communicates through RF, using a TI EZ2500 802.15.4 radio with a frequency range of 2400-2483.5 MHz and 1.2-500 kBaud data rate.

The gateway device 120 also includes a wired connection 216, such as a USB port for connection to a wired network and/or for connection to other processing and display units for integration, configuration and inter-operability purposes.

The gateway device 120 also includes a bank of indicator lights 230, such as LEDs 231-235. As described further below, such lights can be LEDs that indicate a status of the gateway device 120.

The gateway device 120 also includes a power source 214. In one example, the power source 214 is a 1500-1950 mAh Li-Po battery. Other configurations are possible.

In example embodiments, the gateway device 120 utilizes power management techniques that optimize power usage and battery life. For example, when not in use, the gateway device 120 enters a sleep state that involves no active power consumption. Upon waking, the OS of the gateway device 120 is optimized to allow for fast booting to an operating state.

Referring again to FIG. 1, in this example, each of the sensor devices 110 collects data from one or more patients. Such data can include, without limitation, physiological data like temperature, heart rate, blood pressure, oxygen saturation, etc.

In some examples, each of the sensor devices 110 is a computing device that is worn by the individual. Such sensor devices 110 typically include a system memory, a processing unit, a physiological sensor, a radio device, a housing, a printed circuit board, and a power source. Additional details regarding such example sensor devices are described in U.S. patent application Ser. No. 12/827,817 filed on Jun. 30, 2010, the entirety of which is hereby incorporated by reference. Other sensor devices, such as a weight scale, can also be used to measure physiological data.

In this example, an optional wall unit 130 is shown. The wall unit 130 is a computing device positioned in an examination room of a doctor's office or hospital. The wall unit 130 can also be located in other places as well, such as public places like malls or in the patient's home.

The wall unit 130 includes a transceiver that communicates with the gateway device 120 using known techniques, such as Bluetooth and/or WiFi. The wall unit 130 can forward data from the gateway device 120 to the server 170 using the networks 140, 150. In addition, the wall unit 130 can process and display data associated with the data from the gateway device 120, such as text and graphical representations of the data (e.g., blood pressure, temperature, etc.).

The wall unit 130 is optional, in that the gateway device 120 can communicate directly with the server 170 through one or both of the networks 140, 150 when not in range of the wall unit 130. For example, the gateway device 120 can communicate directly with the network 140 using GSM or CDMA, and/or the gateway device 120 can communicate directly with the network 150 using 802.11b/g. Other configurations are possible.

In some examples, the sensor devices 110, the gateway device 120, and the server 170 all communicate using a protocol such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

Referring now to FIGS. 3-6, the gateway device 120 is shown.

A housing 210 of the gateway device 120 is provided in a single color, and all writing on the housing 210 is provided in a contrasting color that is easy to read. In the example shown, the housing is black, and all writing on the housing (e.g., the icons identifying the indicator lights 230) is white. In this manner, it is easy for the user to identify and read the writing when using the gateway device 120. Other configurations, such as Braille to assist users with vision impairment, can also be provided on the housing 210.

The gateway device 120 includes a power button 221 that turns power on and off for the gateway device 120. When powered on, the gateway device 120 communicates with the sensor devices 110, as well as the optional wall unit 130 and/or the networks 140, 150.

In the example shown, the power button 221 is slid along the longitudinal axis of the housing 210 to turn the gateway device 120 on and off. In this example, the power button 221 is recessed within the housing 210 so that the possibility of the power button 221 being accidently actuated is reduced.

The power button 221 can be configured in other manners to reduce inadvertent actuation. For example, the power button could be spring biased into the off position. To turn on, the power button would be slid against the spring force into an on position for a certain period of time (e.g., two seconds) for power on. Other configurations are possible.

The gateway device 120 also includes a port 240 sized to receive a removable storage medium. Examples of such media include SD cards and memory sticks.

The indicator lights 230 are positioned along the housing 210 of the gateway device 120 so that the user can easily view the lights and ascertain the status of the gateway device 120. In some examples, the indicator lights 230 are each a specific color to readily identify the status of the gateway device 120. For example, as shown, the indicator lights are as follows: red LED 235-power up; blue LED 233-connection existing through Bluetooth; yellow LED 231-connection existing through RF radio; white LED 324-connection established through either WIFI radio; and green LED 232-connection established through either 3G radio.

Icons are positioned adjacent to each of the LEDs 231-235 to allow the user to easily determine the status of the gateway device 120. For each, when the LED 232 is lit, the user knows that the Bluetooth radio is actively connected to another device, such as the sensor devices 110. The icons are colored white to contrast with the black of the housing 210 to assist in patient recognition.

In this example, the indicator lights 230 provide the interface for the user. The gateway device 120 does not include any other display or user interface beyond the markings on the housing 210 and the indicator lights 230. In this manner, the gateway device 120 provides a simple interface that can be readily interpreted by the user.

The housing 210 of the gateway device 120 is sized to allow the gateway device 120 to be easily carried by the user. In one example, the housing 210 is approximately 8.6 cm in length by 5.4 cm in width by 0.635 cm in height. Such a size (approximately that of a typical credit card) allows the gateway device 120 to be readily carried in a pocket or wallet/purse. This allows the gateway device 120 to continuously receive data from the body-worn sensor devices 110 and to forward that data to the server 170 as the patient moves. Other configurations and sizes are possible.

Figure 7:
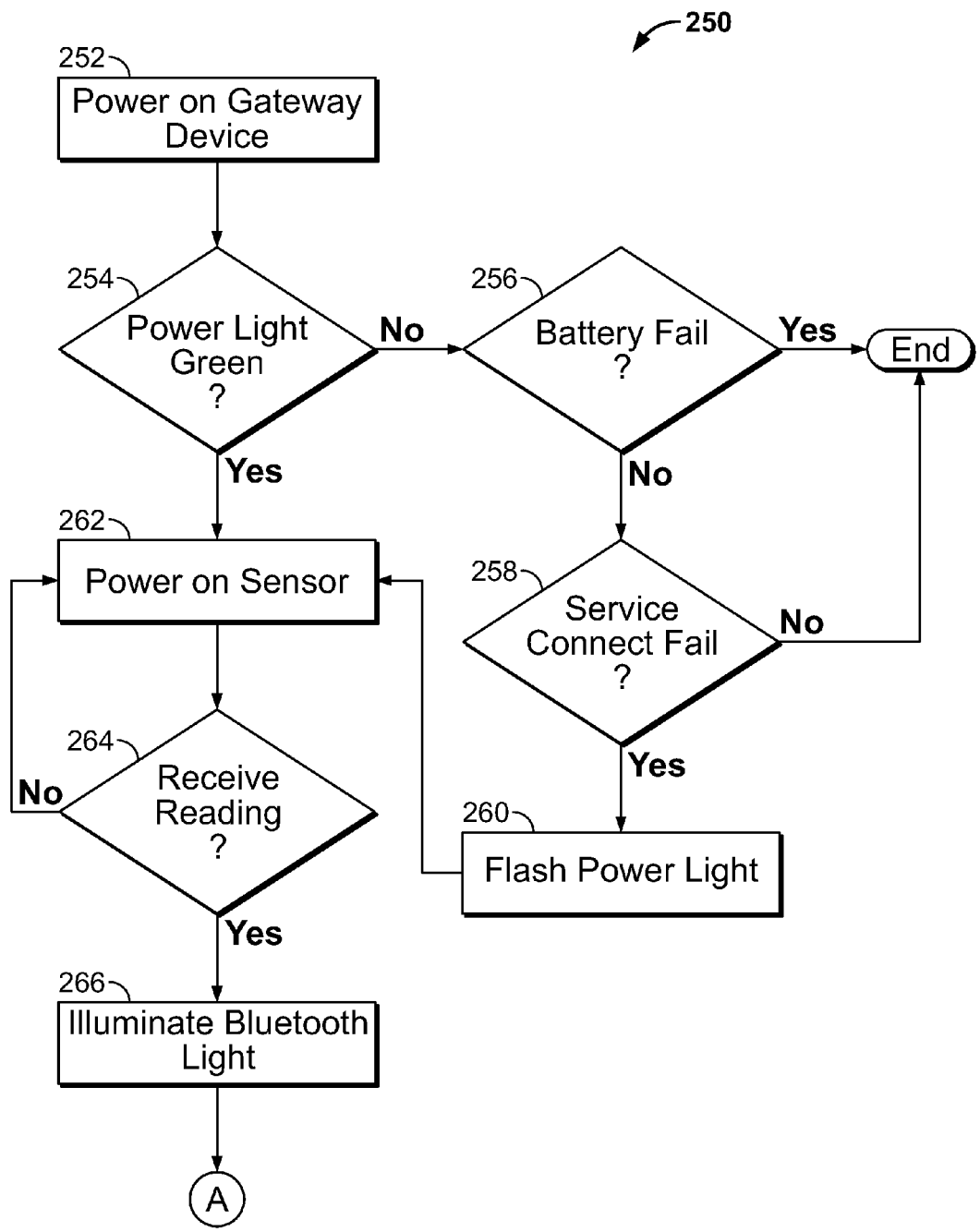
FIG. 7 shows a first portion of an example method for collecting physiological data using the gateway device of FIG. 1.
Figure 8:
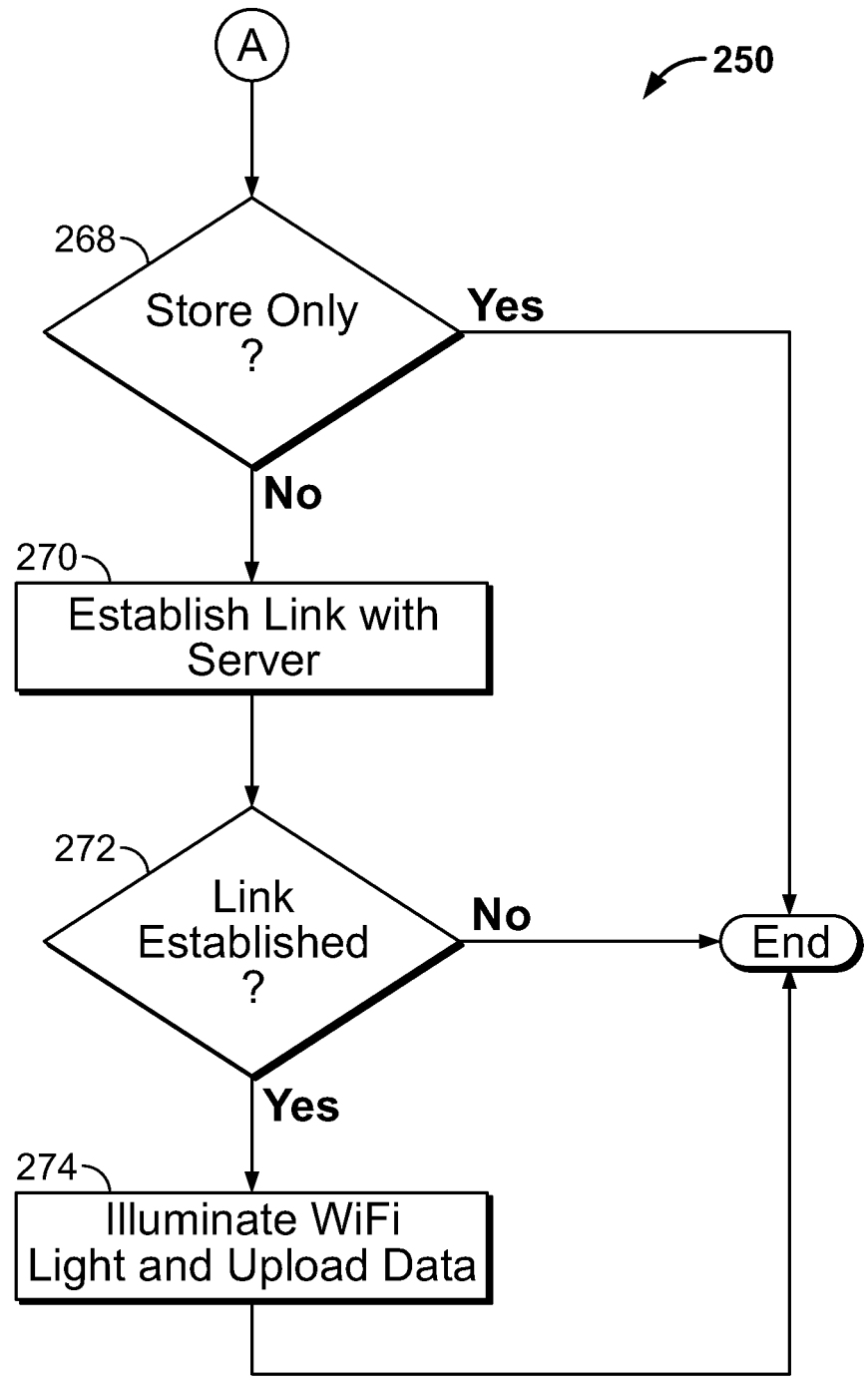
FIG. 8 shows a second portion of the method of FIG. 7.

Referring now to FIGS. 7 and 8, an example method 250 for collecting physiological data using the gateway device is shown.

Initially, at operation 252, the gateway device is powered on. Next, at operation 254, a determination is made regarding whether or not to illuminate the green power light. If the gateway device powers on normally, the green light is lit to indicate power on was successful, and control is passed to operation 262.

Alternatively, if power on is not successful, control is passed to operation 256, and a determination is made regarding whether or not the battery of the gateway device is too low or has failed. If so, the method 250 ends. Otherwise, if not, control is passed to operation 258, and a determination is made regarding whether or not a service connection to the network has been established. If not, the method 250 ends.

If so, control is passed to operation 260, and the power light is illuminated in a manner to allow the user to know that an error has occurred with establishing a connection to the network. For example, the power light can flash and/or be colored differently, such as amber, to indicate the failure. Control is then passed to operation 262.

At operation 262, the sensor is powered on. Next, at operation 264, a determination is made by the gateway device regarding whether or not a reading from the sensor has been received. If not, control is passed back to operation 262 so that the power on the sensor can be cycled.

If so, control is passed to operation 266, and the blue light on the gateway is illuminated to indicate that a Bluetooth link has been established with the sensor.

Next, at operation 268 (see FIG. 8), a determination is made regarding whether the data from the sensor should be stored or forwarded. If the data is to be stored on the local memory of the gateway for future forwarding (e.g., if the link to the network is currently unavailable), the method 250 ends.

If not, control is passed to operation 270, and the gateway device attempts to establish a link through the network to the server. Next, at operation 272, a determination is made regarding whether or not the link was established. If not, the method 250 ends. If so, control is passed to operation 274, and the appropriate light on the gateway device (e.g., the white WiFi light is lit), and the data is uploaded by the gateway device to the server.

Figure 9:
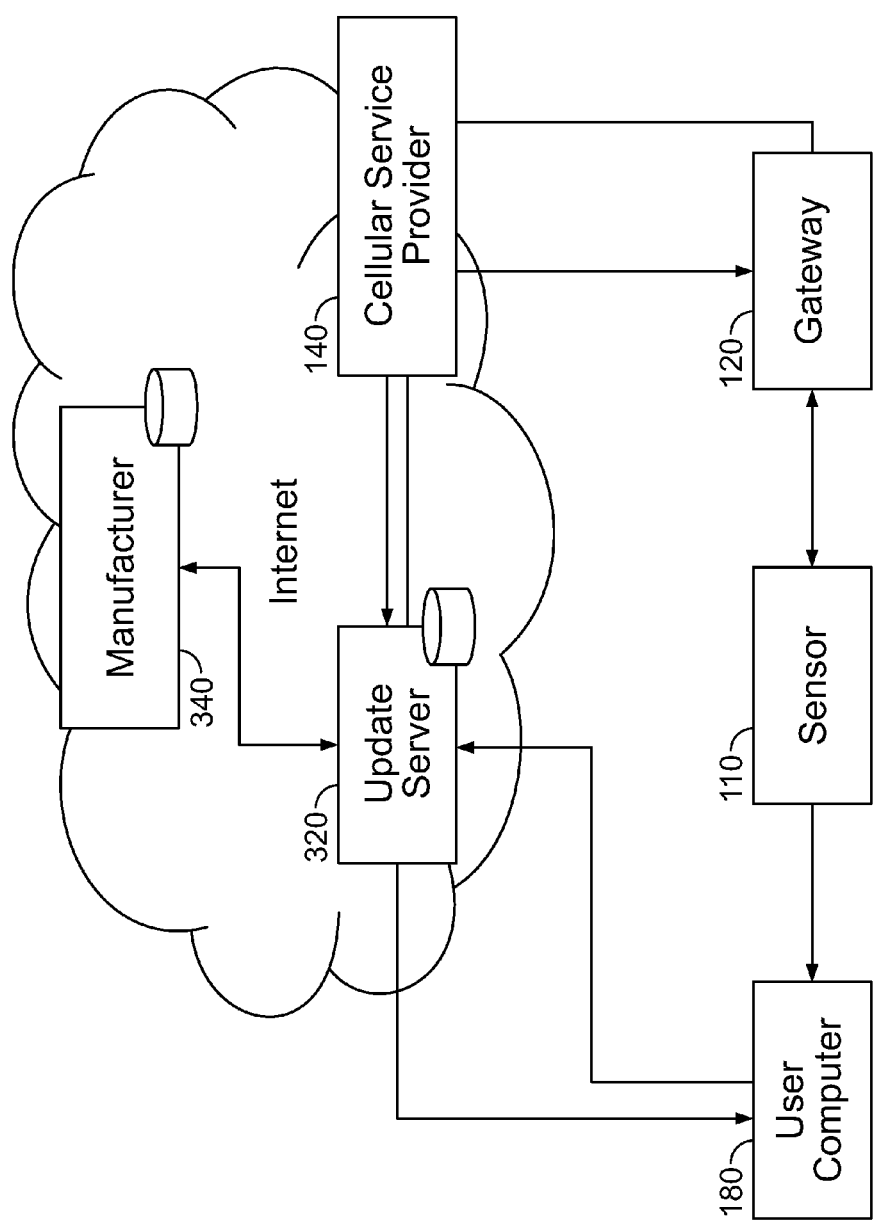
FIG. 9 shows an example system for updating the gateway device of FIG. 1 to communicate with a new sensor device.

Referring now to FIG. 9, in some examples, the gateway device 120 can be programmed to communicate with new sensor devices 110 while in the field, such as in use by the patient.

Such a process is initiated by the user connecting to an update server 320 using a computing device 180. For example, the user can browse to a specific web site using a browser. See, e.g., FIG. 17. The user then enters a sensor ID provided on the product packaging or other literature associated with the new sensor device 110. The ID is an encoded number based on various parameters, such as the original equipment manufacturer and device type.

Once entered, the ID is sent to the update server 320. At this point the ID is resolved to a device class, and the manufacturer's information is identified. The update server 320 thereupon queries a manufacturer portal 340 associated with the manufacturer of the sensor device 110 to determine the MAC address of the sensor device 110 and the protocol version. Once obtained by the update server 320, the MAC address and protocol information (e.g., the message exchange sequences and the respective message formats) is passed to the gateway device 120.

The gateway device 120 thereupon attempts to establish communication with the sensor device 110 using the MAC address and protocol encoding received from the update server 320 and requests the sensor device 110 to send a reading. If a response is received from the sensor device 110, the gateway device 120 strips out the expected value fields from the received message and transmits those fields back to the update server 320. The update server 320 validates the response against the expected values for that class of sensors and notifies the results on the user's computing device 180. If successful, the gateway device 120 can begin communicating with the new sensor device 110 to collect and forward data to the server 170.

Figure 10:
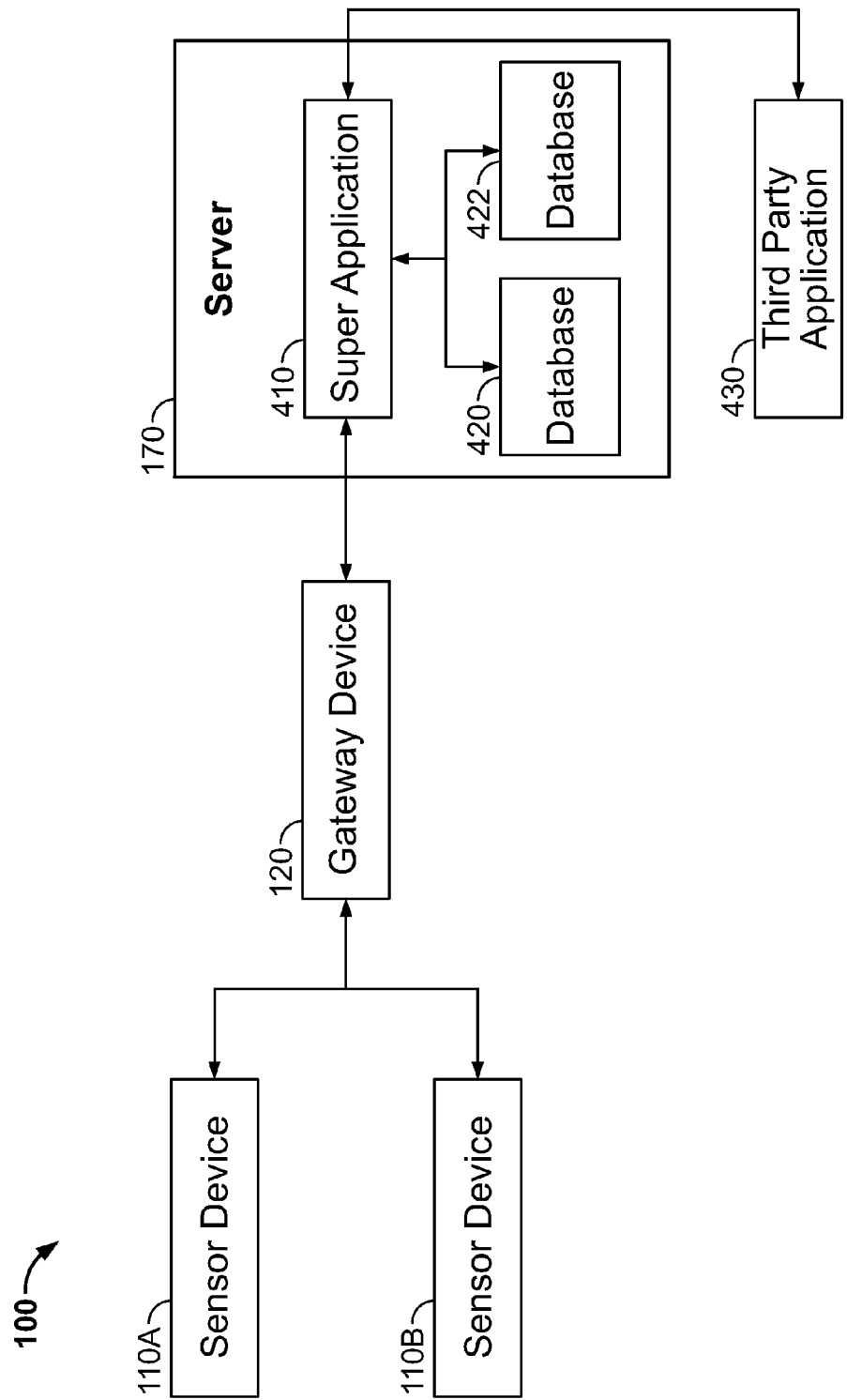
FIG. 10 shows another view of the system of FIG. 1.

Referring now to FIG. 10, additional details regarding the server 170 are shown.

The server 170 includes one or more computing devices. The server 170 executes a super application 410 that is specific for each user of the system 100. For example, as depicted, the user has two body-worn sensor devices 110A, 110B. Each of these sensor devices 110A, 110B communicates with the gateway device 120. The gateway device 120, in turn, forwards the data from the sensor devices 110A, 110B to the server 170.

Upon receipt, the data is routed to the super application 410 associated with the user based on a unique user identifier that is communicated with the data from the gateway device 120. The super application 410 maintains meta information regarding each sensor device that generates the data for the user. Upon receipt of the data, the super application 410 determines, based on the meta information, where the data should be stored.

For example, in this embodiment, there are device-specific repositories 420, 422 for each of the sensor devices 110A, 110B. When the super application 410 receives data from the gateway device 120 that originates from the sensor device 110A, that data is forwarded by the super application 410 to the database specific to that device (e.g., database 420) for storage. On a similar note, when the super application 410 receives data from the gateway device 120 that originates from the sensor device 110B, that data is forwarded by the super application 410 to the database 422 for storage.

The super application 410 controls all access to the data stored for the user. For example, the super application 410 retains the meta information about where the data is stored, and the super application 410 requires authentication before the super application 410 provides access to the data.

The super application 410 allows data movement between application suites that are installed for a particular user. The super application 410 also facilitates data movement across user profiles. The super application 410 has the authority to act as a proxy on behalf of the user and negotiate data exchange transactions with other super application entities.

To initiate a data exchange, the requesting entity sends out a message comprising of an authentication token, the type of data requested (e.g., weight readings), and the number of data items requested. On receiving this sequence, the super application 410 validates the token against a white list of acceptable tokens. If the token in invalid, it generates a notification for the user informing them about this request.

On receipt of a valid token, the super application 410 proceeds to locate a database containing the type of data requested. Notifications are sent out if such a database is not found and the incoming request is denied. Otherwise, the requested number of items is fetched from the relevant database and the request is serviced. Thus this framework eliminates the need for applications to know about the specific details of the databases, especially when the databases are residing in another user's profile.

For example, a third party application 430 (see FIGS. 15 and 16) can request data for a patient from the server 170. Such a request is routed to the super application 410 for that particular user. The super application 410 first determines whether or not the third party application 430 can provide the proper credentials to obtain the data. For example, the super application 410 can require a username and password for authentication before access is given.

If the proper credentials are provided, the super application 410 queries the proper database 420, 422 (for example, if the third party application 430 requests data from the sensor device 110A, the super application 410 would query the database 420) to obtain the data. Once obtained, the super application 410 sends the data to the third party application 430.

Figure 11:
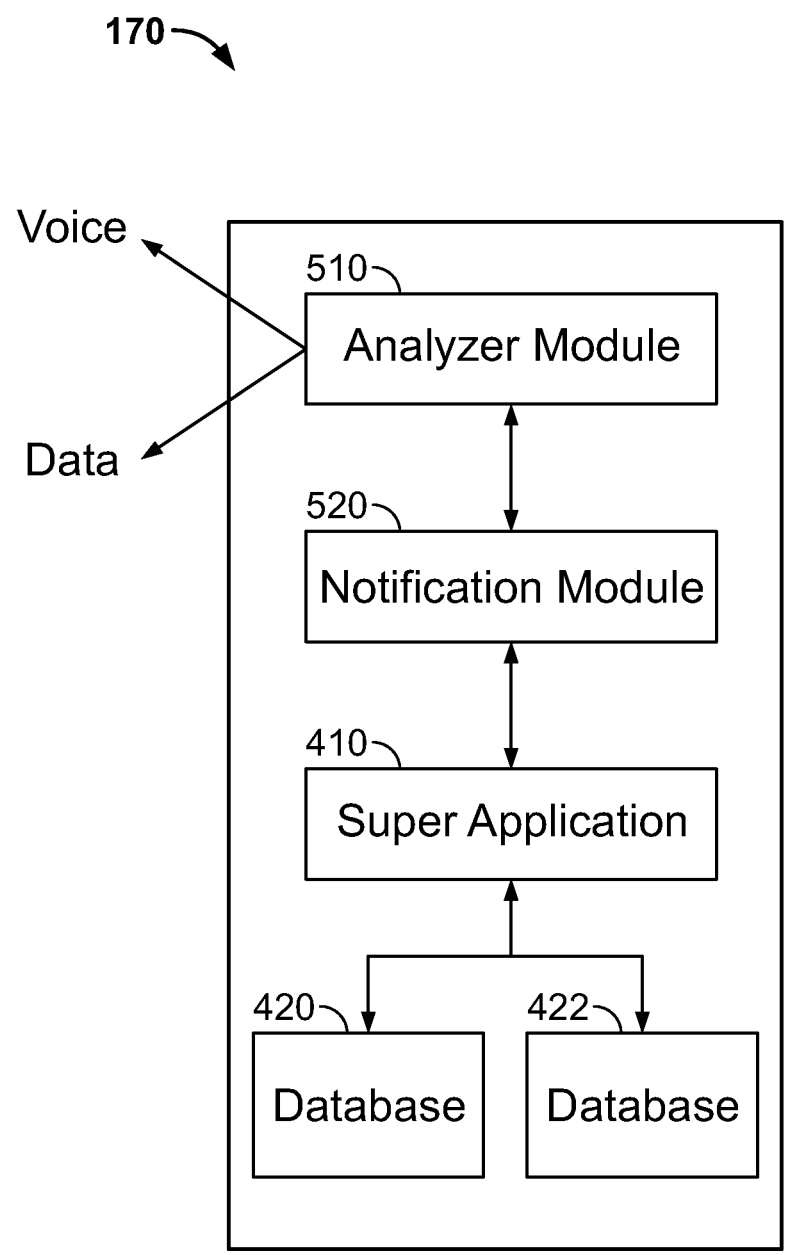
FIG. 11 shows a view of the server of the system of FIG. 1.

Referring now to FIG. 11, the server 170 is shown in more detail.

In this example, the server 170 is programmed to provide automatic and configurable medical device data notifications, the parameters of which can be determined by the patient or clinician.

For example, the server 170 includes an analyzer module 510 that communicates with the super application 410 to obtain data about the patient. The analyzer module 510 can be invoked by the reception of a new value from the gateway device 120. Exemplary devices and/or values can include blood pressure readings, temperature reading, blood glucose levels, weight, blood oxygen saturation, blood hemoglobin levels, blood hematacrit levels, ECG readings, heart rate, and any subjective reading communicated or provided by the patient.

The analyzer module 510 is configured to communicate with a notification module 520 based on received data and logical analysis of database parameters. Once invoked, the notification module 520 communicates with the super application 410 to retrieve the data from the databases 420, 422. The analyzer module 510 instructs the notification module 520 to provide notifications based on the configuration set by the doctor, nurse, and/or patient. The notifications can be provided in a variety of formats, including voice and data (e.g., SMS, MMS, e-mail, phone call or any other personal communication medium) and can be configured regarding to whom the notifications are provided (e.g., care provider, doctor, patient, and/or relative). See FIG. 12.

Other parameters are also configurable, such as frequency of notification, follow-up if receipt is not confirmed, and content of notification based on recipient type (doctor versus family member, e.g.). Further, a web-based portal can be used to fully configure the analysis and/or notification modules 510, 520.

In one embodiment, the notification module 520 maintains a user account table. For each user, a table of active applications is used to define the applications the user has activated. See FIGS. 15 and 16 regarding the various applications that are provided to the user. For each user application combination, a table is used to point to one or many analyzer scripts that may or may not be invoked in the analyzer module 510 on reception of a new result. For each analyzer script, a database table parameter is used to point to a notification group, which can be a single individual or multiple individuals. For each notification group defined in the notification module 520, there are one to many phone numbers and emails configured to receive the results of the clinical analyzer.

For example, the following data table defines the structure of configuration for facilitating this ability.

Apps

| AppKey | Type |
|---|---|
| 1 | weight |
| 2 | pain |
| 3 | glucose |
| 4 | bloodpressure |

User Account

| Accountkey | USERNAME | AcntDetail1 | AcntDetail2 |
|---|---|---|---|
| 1 | jimdello@myemail.com | 12 Maple st | NY |
| 2 | harrishmugun@mymail.com | 14 Walnut st | NY |

Account Apps

| UserApp | AccountKey | AppKey | Share | DefaultText |
|---|---|---|---|---|
| 1 | 1 | 1 | True | 'user' has taken a weight reading of 'value' |
| 2 | 1 | 2 | True | 'user' has record a pain level 'value1' in the 'value2' |
| 3 | 2 | 1 | True | 'user' has taken a weight reading of 'value' |

Apps Clinical Analyzer(s)

| ClinAnalysisKey | Accountkey | AppKey | Analyzer | Active | Share | NotificationGroup |
|---|---|---|---|---|---|---|
| 1 | 1 | 1 | CHFWeight.js | True | True | 1-1 |
| 2 | 1 | 1 | WeightLoss.js | False | True | 1-2 |
| 3 | 1 | 2 | CHFPain.js | True | False | 1-3 |
| 4 | 2 | 1 | WeightLoss.js | True | True | 2-1 |

Clinical Analysis Notification

| NotificationKey | Group | MMS | SMS | EMAIL | Number | Email | Type |
|---|---|---|---|---|---|---|---|
| 1 | 1-1 | False | True | False | 315-555-1234 | Null | PVT |
| 2 | 1-1 | False | True | True | 315-555-5555 | psoderberg@doctor.com | MD |
| 3 | 1-1 | False | False | True | null | janedello@mymail.com | REL |
| 4 | 1-2 | False | True | False | 315-555-1234 | Null | REL |
| 5 | 1-2 | False | True | True | 315-555-5555 | psoderberg@doctor.com | MD |

-continued

| NotificationKey | Group | MMS | SMS | EMAIL | Number | Email | Type |
|---|---|---|---|---|---|---|---|
| 6 | 1-3 | False | True | True | 315-444-4321 | marydello@mymail.com | REL |
| 7 | 2-1 | False | True | True | 315-555-5555 | psoderberg@doctor.com | MD |
| 8 | 2-1 | False | True | True | 213-234-5678 | janemugun@mymail.com | REL |
| 9 | 2-1 | False | True | False | 789-555-1234 | Null | PVT |

In the tables: ACT=the account holder (the patient); MD=the doctor(s) or medical professional; REL=network relation or family member.

In another embodiment, additional analyzer scripts are included in the "application" or suite packages that can be selected by the patient or caregiver. See FIGS. 15 and 16. These analyzers can be specific depending on the types of sensor devices being used. For example, there may be an application associated with the congestive heart failure (CHF) suite of devices that can be configured to automatically engage the notification module 520 when a patient's weight scale readings deviate from the previous reading by a specified amount. The analyzer module 510 can be further configured to predict disease states and/or suggest a new application and/or medical device and transmit associated analysis to the care provider.

Over time, multiple new and varied analysis types might be added expanding the clinical advice or decision support that can be offered to the clinician or provider. Upon analysis of a device reading by one or many configured analysis packages, the result of one or many results may or may not invoke one or many configurable notification systems that can send one or many types of messages to a one or many individuals mobile phone via SMS text or MMS pictures, email text and pictures, a pager, or any other personal communication medium.

Such a notification system is advantageous for several reasons. For example, different levels can be defined which have different types of notifications to customize the notifications. Further, the number of people to whom notifications are sent and types (format and pattern) of messages being sent are fully configurable.

Referring now to FIGS. 12-19, an example interface 500 for accessing data stored on the server 170 is shown. The interface 500 can be accessed over the Internet using a browser on the computing device 180. The interface 500 can be configured for use by the caregiver, the patient, or another interested party such as a relative.

The configuration for the interface 500 can be tailored based on the user's goals. For example, a patient can find, store, and review data about the patient's health, while a caregiver can review data from a plurality of patients.

Figure 12:
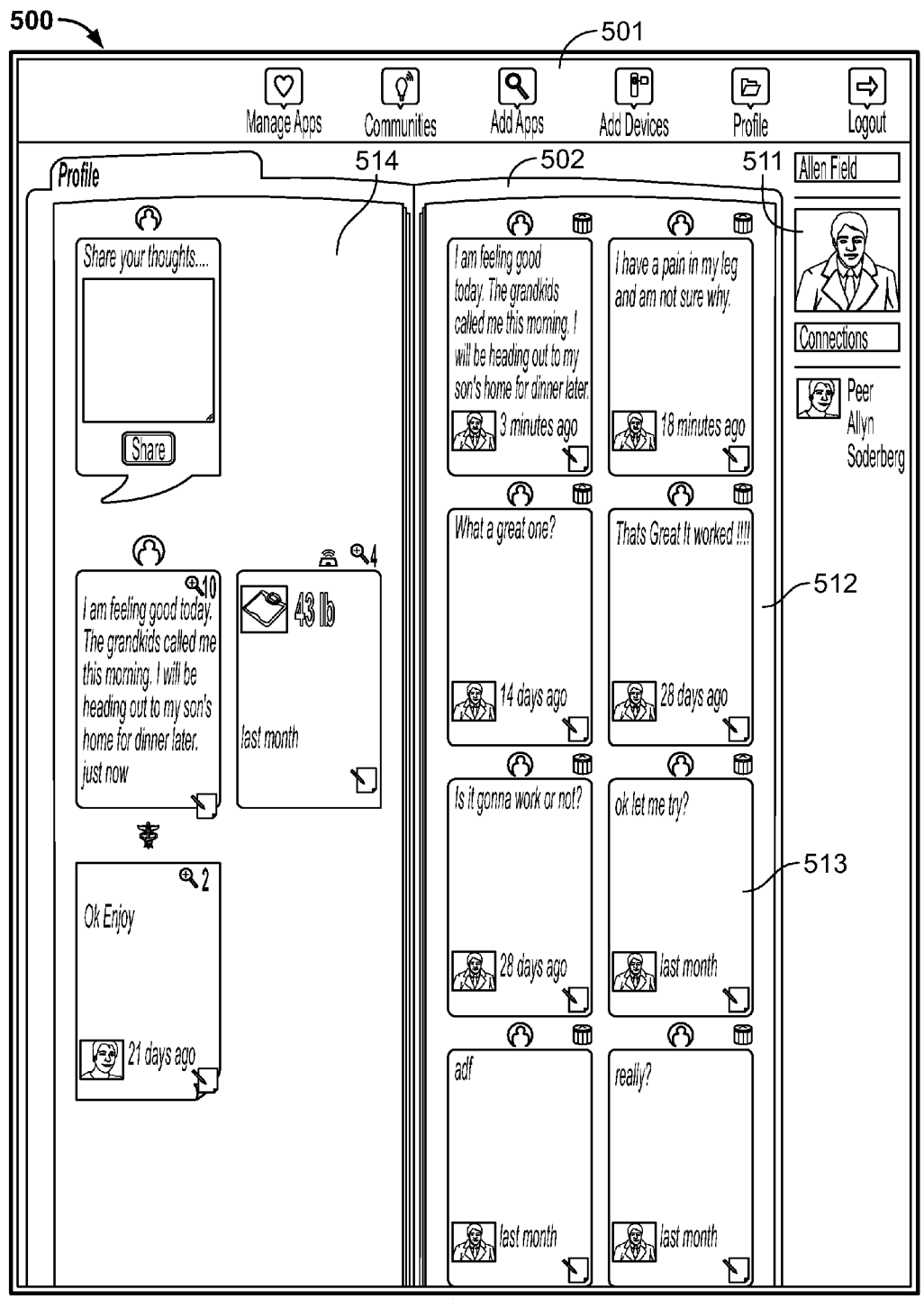
FIG. 12 shows an example user interface for accessing data associated with the system of FIG. 1.

In FIG. 12, the interface 500 includes a profile screen that displays aspects of the user's profile. For patients, the interface 500 includes a toolbar 501 that allows the patient to access different functionality, including applications associated with the user's profile, details about sensor devices associated with the patient, and profile information.

The interface 500 also includes an identification menu 511 including bibliographic information like the patient's name and picture. The menu 511 also provides a list of connections to others on the system 100, such as friends, caregivers, patients, etc. Messages can be passed between users that are connected to one another, such as inspirational messages between patients or medical information from a doctor to a patient. See FIG. 14. Additional information, such as contact information and health-related information, can also be accessed.

The interface 500 further includes a notebook or file portion 502 that is configured to display different information to the user depending on the user selection. In this example, the notebook portion 502 includes a first section 512 including a plurality of "sticky" notes 513 populated with comments from the patient. The notes 513 can include any content desired by the patient, such as feelings and inspirational sayings.

The notes 513 can be moved around and placed at different spots on the notebook portion 502, can be overlapped on one another, and can be deleted. A second section 514 of the notebook portion 502 also includes notes and other information populated by the user and the user's connections.

Figure 13:
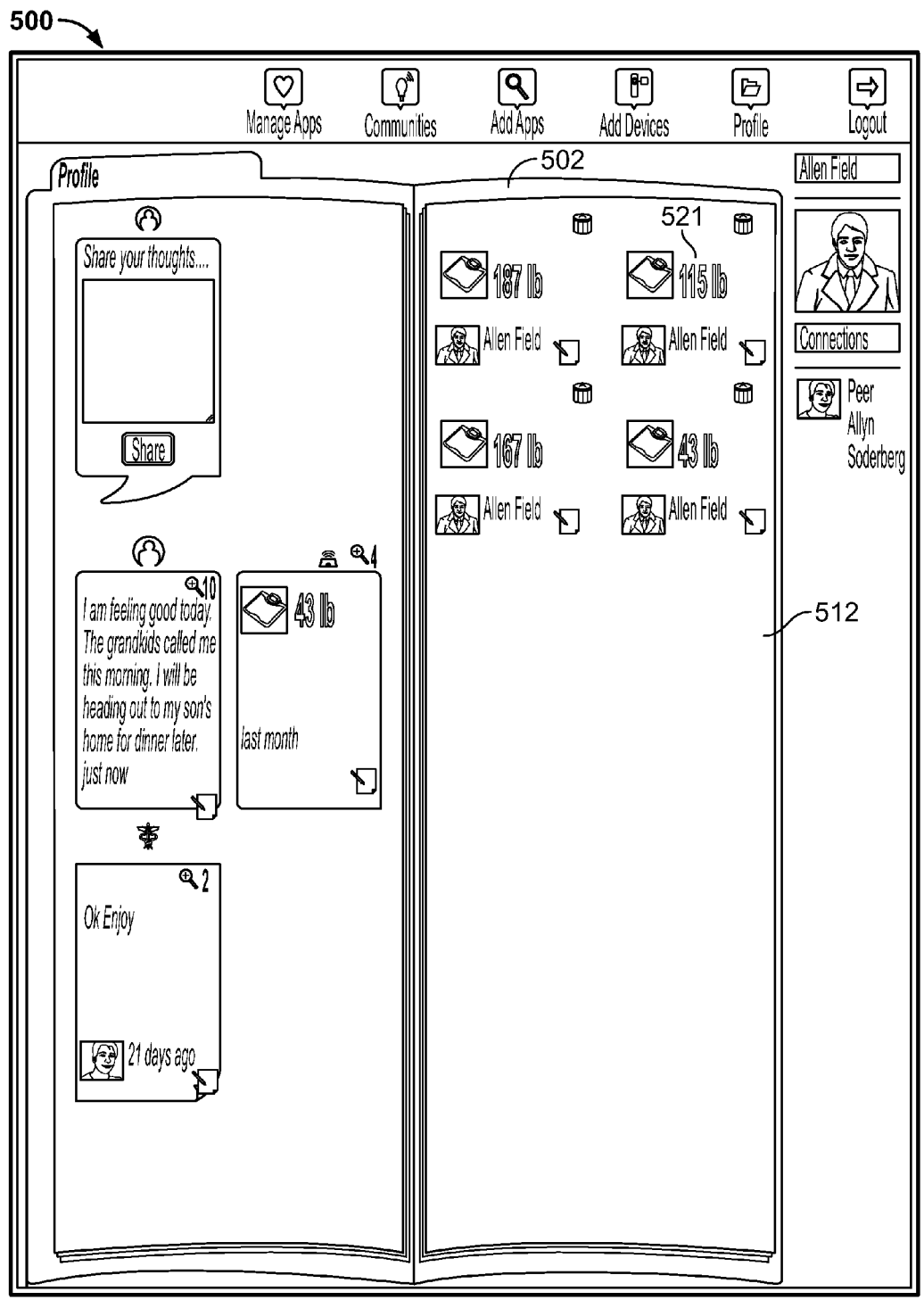
FIG. 13 shows another example user interface for accessing data associated with the system of FIG. 1.

In FIG. 13, the first section 512 includes a plurality of readings 521 associated with the patient. The readings 521 can include any physiologic readings associated with the patient such as, for example, weight readings collected using the sensor devices 110 and the gateway device 120.

Figure 14:
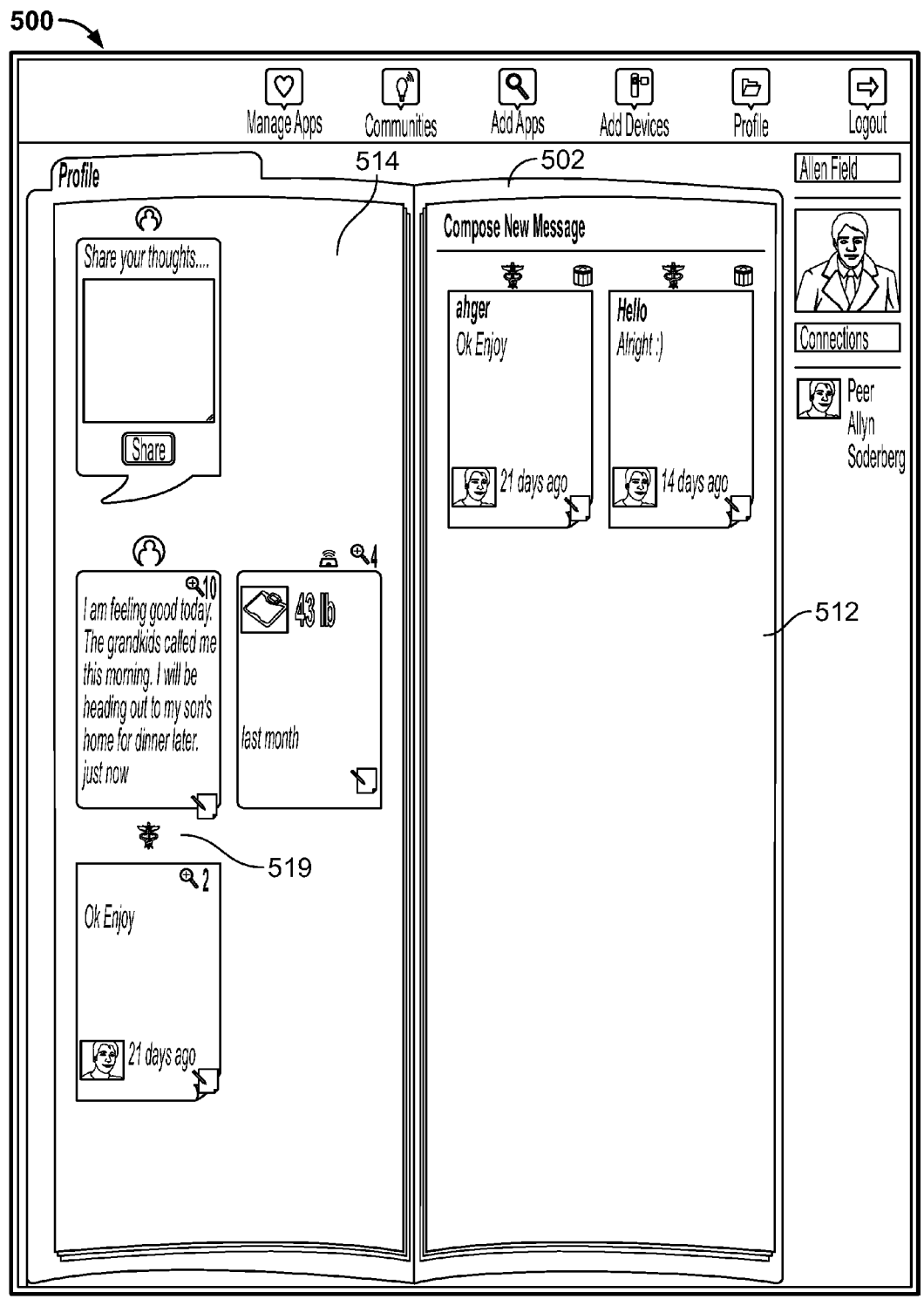
FIG. 14 shows another example user interface for accessing data associated with the system of FIG. 1.

In FIG. 14, the first section 512 of the interface 500 includes messages that have been exchanged between the user and the user's connections on the system 100. In addition, the messages can include notifications from the notification module 520. The messages are displayed as sticky notes that can be moved and deleted as desired.

In some examples, the messages are color-coded for easy recognition. For example, the notes that are blue are from the doctor or other clinical professionals. If the user clicks a pile of message 519 located on the second section 514 that is blue, all of the blue messages from the doctor are shown on the first section 512. Other example colors include: orange for medical device or subjective symptoms; green for comment threads started by the patient; and yellow for messages from relatives and friends. Other schemes can be used.

In some examples, the population and placement of the notes on the first and second sections 512 is automated. This process includes verification of the authenticity of an incoming request for a particular page for the notebook portion 502. If the request is from a valid user in a valid session, the screen geometry that is available for displaying the messages is analyzed. This information is retrieved from a message database, which acts as a persistent store for all messages intended for the user. For each message, a suitable template is selected based on the message type and screen geometry. This template is populated with the corresponding message and a visual object is created. On completion, a matrix including the location information for each visual object, relative to the screen real estate, as well as the object type is returned.

Each note can contain a plurality of information, including a signature of an application generating the note or a picture of a user if the note is a message. The note can also include recorded values and timestamps defining the time the values were recorded and the time the note was posted in the notebook. Other configurations are possible.

Figure 15:
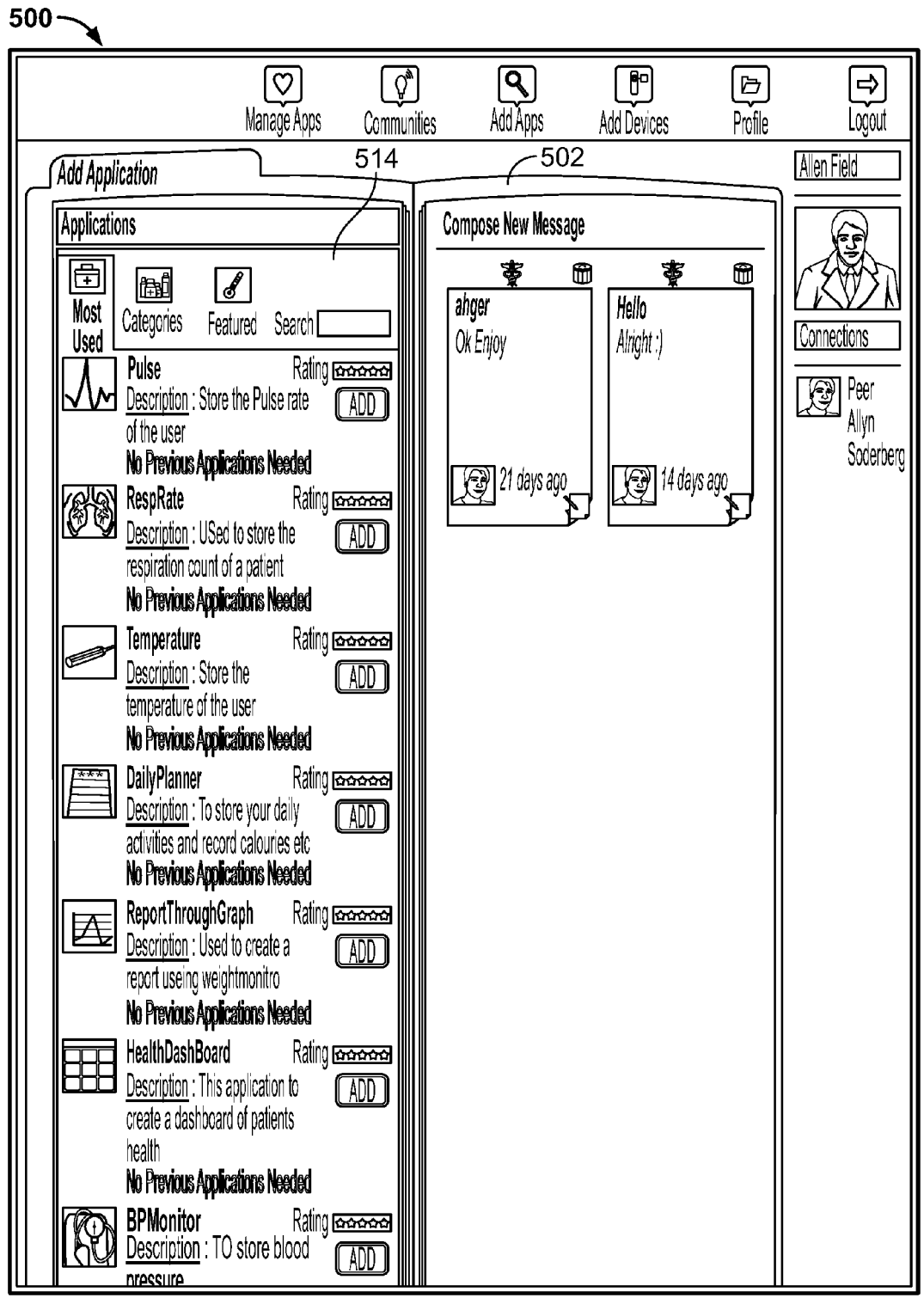
FIG. 15 shows another example user interface for accessing data associated with the system of FIG. 1.
Figure 16:
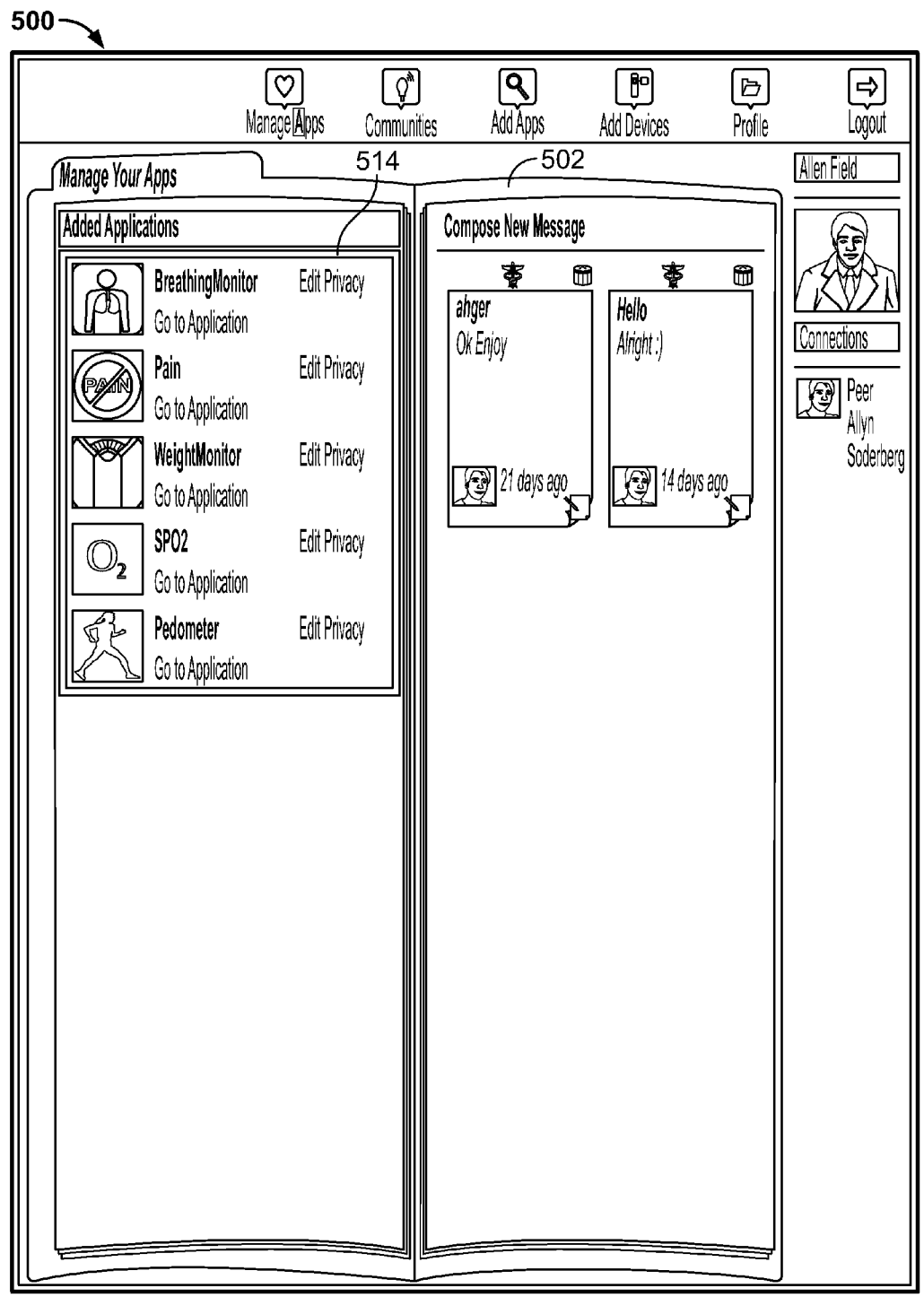
FIG. 16 shows another example user interface for accessing data associated with the system of FIG. 1.

Referring now to FIGS. 15-17, the user can access a plurality of applications listed on the second section 514.

These applications, when selected, can be used to manipulate the data collected by the system 100 and to provide the user with more information based on the data. For example, applications including topics like pulse, respiratory rate, temperature, etc., can be selected by the user.

Once selected, the user can manage the applications in the section 514. See FIG. 16. The selected applications can be deleted or privacy policies for each application defined. For example, in FIG. 17, an interface 530 is provided that allows the user to define the privacy policies for each selected application. The interface 530 allows the user to define how the application communicates with the user, including through SMS, email, and/or a feed. By checking the boxes associated with each mode of communication, the user authorizes the application to use that mode of communication.

Figure 18:
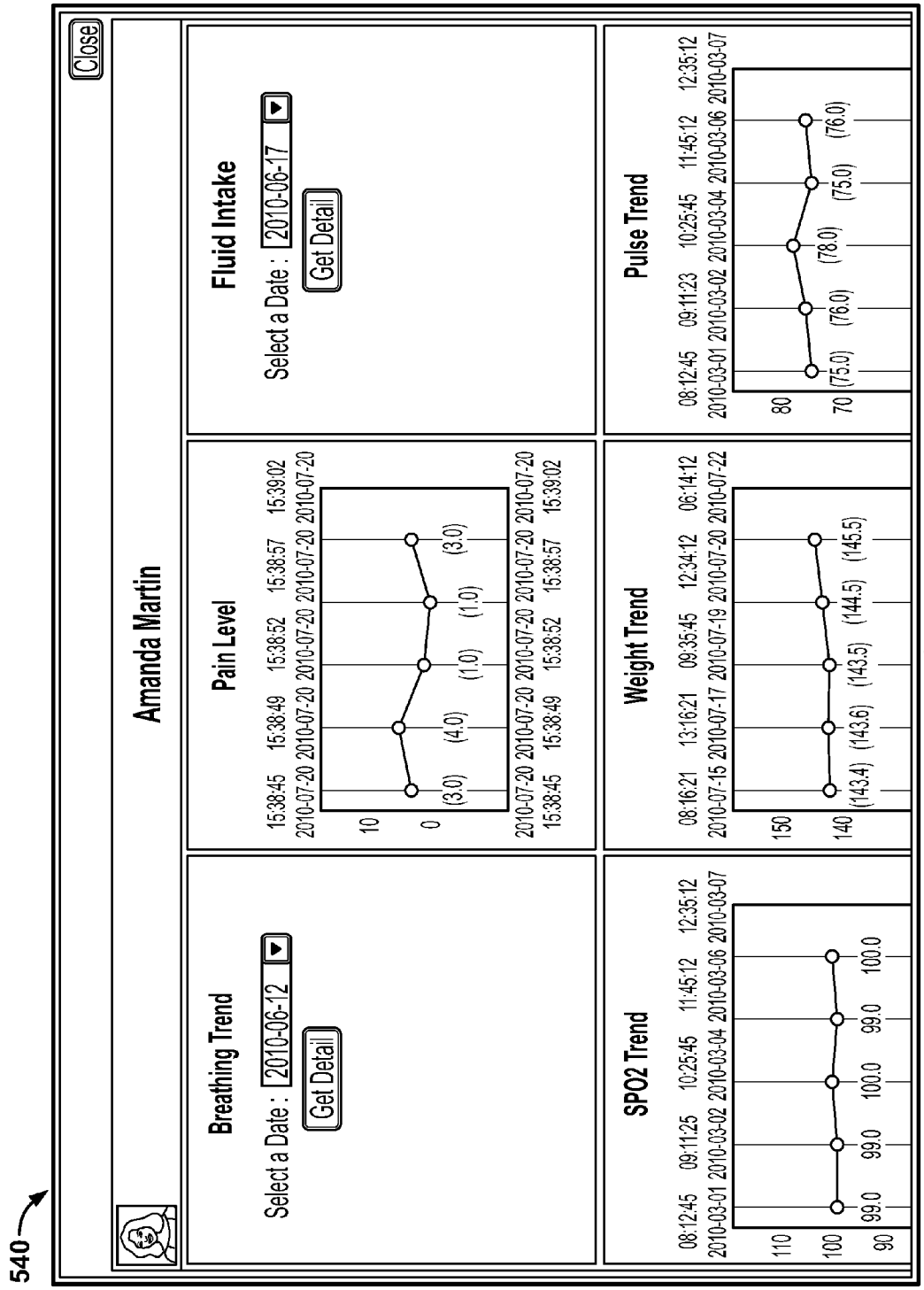
FIG. 18 shows another example user interface for accessing data associated with the system of FIG. 1.

Referring now to FIG. 18, the output from a plurality of the applications is shown in an interface 540. Examples of the output include trends and data at specific times. The information to create the trends and specific times was pulled from the server 170, and the user's applications manipulate the data to provide the information. Other configurations are possible.

Figure 19:
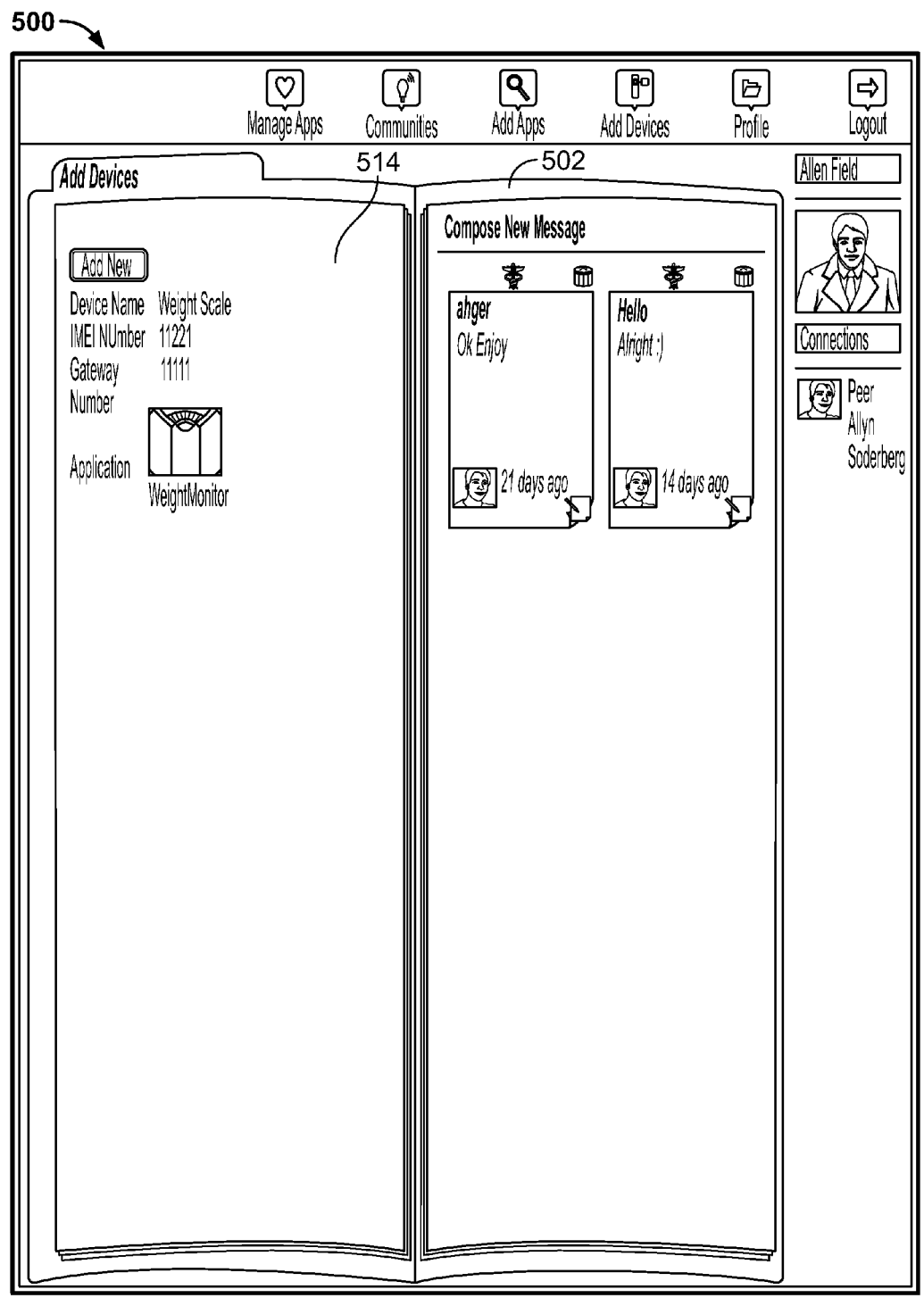
FIG. 19 shows another example user interface for accessing data associated with the system of FIG. 1.

FIG. 19 shows the section 514 of the notebook portion 502 including information about the sensor devices 110 that are associated with the user. For example, the section 514 lists a weight sensor, including the name of the sensor, product number, and gateway number corresponding to the gateway device 120. Any applications associated with the sensor device are also listed.

The various embodiments described above are provided by way of illustration only and should not be construed as limiting. Those skilled in the art will readily recognize various modifications and changes that may be made without following the example embodiments and applications illustrated and described herein, and without departing from the true spirit and scope of the disclosure.

What is claimed is:

1. A system for storing data collected by a body-worn sensor, the system comprising:
    a central processing unit (CPU) that is configured to control operation of a gateway device; and
    one or more computer readable data storage media storing software instructions that, when executed by the CPU, cause the gateway device to:
        receive a MAC address of a new sensor and a protocol version associated with the new sensor from a server, the server being in communication with a manufacturer portal having access to the MAC address of the new sensor and the protocol version associated with the new sensor;
        attempt to contact the new sensor using the protocol version and the MAC address;
        when a response is received, send the response to the server for validation;
        when the response is validated by the server, establish communications with the new sensor; and
        forward data from the new sensor to a second server, the second server being different from the server, wherein the second server includes a super application associated with a user of the new sensor, with the super application being programmed to control access to the data by causing the second server to:
        receive a request from another application for access to the data, the request including an authentication token;
        validate the authentication token against a white list of acceptable tokens; and
        permit access to the data by the another application upon validation of the authentication token.

2. The system of claim 1, wherein the super application identifies a database in which the data from the new sensor is stored.

3. The system of claim 2, wherein the super application identifies a plurality of databases in which data from a plurality of sensors associated with the user is stored.

4. The system of claim 1, further comprising a notification module programmed to generate a notification to a user when the data meets a certain criteria.

5. The system of claim 4, wherein the notification module is programmed to notify a plurality of individuals when the data meets a second criteria.

* * * * *